United States Patent
Kamon et al.

(10) Patent No.: US 12,409,004 B2
(45) Date of Patent: Sep. 9, 2025

(54) MASTER-SLAVE SYSTEM AND CONTROLLING METHOD

(71) Applicant: Kawasaki Jukogyo Kabushiki Kaisha, Kobe (JP)

(72) Inventors: Masayuki Kamon, Kobe (JP); Hiroki Takahashi, Kobe (JP); Kai Shimizu, Kobe (JP); Yuki Takayama, Kobe (JP); Jun Fujimori, Kobe (JP); Hiroki Kinoshita, Kobe (JP); Masahiko Akamatsu, Kobe (JP); Takanori Kozuki, Kobe (JP)

(73) Assignee: KAWASAKI JUKOGYO KABUSHIKI KAISHA, Kobe (JP)

( * ) Notice: Subject to any disclaimer, the term of this patent is extended or adjusted under 35 U.S.C. 154(b) by 269 days.

(21) Appl. No.: 17/776,606

(22) PCT Filed: Nov. 13, 2020

(86) PCT No.: PCT/JP2020/042379
§ 371 (c)(1),
(2) Date: May 13, 2022

(87) PCT Pub. No.: WO2021/095833
PCT Pub. Date: May 20, 2021

(65) Prior Publication Data
US 2022/0401169 A1     Dec. 22, 2022

(30) Foreign Application Priority Data
Nov. 15, 2019    (JP) ................................. 2019-207272

(51) Int. Cl.
*A61B 34/37*     (2016.01)
*B25J 13/08*     (2006.01)
(Continued)

(52) U.S. Cl.
CPC ............... *A61B 34/37* (2016.02); *B25J 13/08* (2013.01); *G01B 11/02* (2013.01); *G01B 11/026* (2013.01);
(Continued)

(58) Field of Classification Search
CPC ... A61B 34/37; B25J 13/08; B25J 3/00; B25J 9/1692; B25J 9/1697; B25J 9/1689;
(Continued)

(56) References Cited

U.S. PATENT DOCUMENTS 4,954,762 A * 9/1990 Miyake .............. G05B 19/4182
                                                          700/190
5,833,762 A * 11/1998 Wanner .................. B25J 9/1692
                                                             134/123
(Continued)

FOREIGN PATENT DOCUMENTS

JP         2009-274191 A      11/2009

OTHER PUBLICATIONS

Laura M. Hiatt et al. "Coordinate Frames in Robotic Teleoperation", Intelligent Robots and Systems, 2006 IEEE/RSJ International Conference on, IEEE, PI, International Conference on Intelligent Robots and Systems, Oct. 9-15, 2006, pp. 1712-1719, Beijing, China.

*Primary Examiner* — Jonathan M Hansen
(74) *Attorney, Agent, or Firm* — XSENSUS LLP

(57) ABSTRACT

A master-slave system includes a master unit, a slave unit, and a control device. The control device includes first circuitry that determines a first relationship that is a relationship between a slave coordinate system and an object coordinate system, second circuitry that determines a second relationship that is a relationship between a master coordinate system and the object coordinate system, and third circuitry that outputs an operational command for causing the slave unit to operate according to operational informa-
(Continued)

tion of the master unit, the first relationship, and the second relationship. When the object coordinate system is moved, the first circuitry newly determines the first relationship after the movement based on the moved object coordinate system and the slave coordinate system, and the second-circuitry determines the second relationship after the movement, as a relationship similar to the second relationship before the movement.

14 Claims, 10 Drawing Sheets

(51) Int. Cl.
G01B 11/02 (2006.01)
G01B 11/03 (2006.01)
G01B 11/14 (2006.01)
B25J 3/00 (2006.01)

(52) U.S. Cl.
CPC ............. *G01B 11/03* (2013.01); *G01B 11/14* (2013.01); *B25J 3/00* (2013.01)

(58) Field of Classification Search
CPC ...... B25J 13/025; G01B 11/02; G01B 11/026; G01B 11/03; G01B 11/14
See application file for complete search history.

(56) References Cited

U.S. PATENT DOCUMENTS

| | | | |
|---|---|---|---|
| 11,741,632 B2* | 8/2023 | Mizohana | G06T 7/0004 348/159 |
| 2011/0046782 A1* | 2/2011 | Fixell | G05B 19/4015 700/251 |
| 2019/0193243 A1* | 6/2019 | Akiyama | B25J 9/0096 |
| 2022/0028117 A1* | 1/2022 | Mizohana | G06T 7/80 |
| 2022/0410375 A1* | 12/2022 | Tsuboi | G01B 11/005 |

* cited by examiner

MASTER-SLAVE SYSTEM AND CONTROLLING METHOD

CROSS-REFERENCE TO RELATED APPLICATIONS

This application is based on PCT filing PCT/JP2020/042379, filed Nov. 13, 2020, which claims the priority of Japanese Patent Application No. 2019-207272 filed on Nov. 15, 2019, in Japan Patent Office, which is incorporated as a part of this application by reference in the entirety.

TECHNICAL FIELD

The present disclosure relates to a master-slave system and a controlling method.

BACKGROUND ART

Conventionally, robots have been used in order to substitute human acts. For example, Patent Document 1 discloses an industrial robot which corrects a teaching point which is remotely instructed. The industrial robot can perform a coordinate conversion from a robot coordinate system to a workpiece coordinate system, and its reversed conversion, and correctively change the remotely-instructed teaching point into a nearest lattice point in virtual space grids which are set beforehand to the workpiece coordinate system. The industrial robot has a function for regulating itself to stop at the lattice point.

REFERENCE DOCUMENT OF CONVENTIONAL ART

Patent Document

[Patent Document 1] JP2009-274191A

DESCRIPTION OF THE DISCLOSURE

For example, when performing a work to apply an action, such as grinding, to a curved surface of an object by using the robot, the position and the posture of a target area change with progress of the work. An operator of the robot operates a user interface corresponding to the change in the position and the posture of the target area. For example, when the posture of the target area changes greatly, the operator may need to operate the user interface in a difficult posture. Therefore, it becomes difficult for the operator to operate the user interface.

One purpose of the present disclosure is to provide a master-slave system and a controlling method, in which operation of a master unit, such as a user interface, is easy, even when a target to which a slave unit, such as a robot, applies operation is changed.

In order to achieve the purpose, a master-slave system according to one aspect of the present disclosure includes a master unit including an operation end, and an operation detector that detects operational information that is information inputted by a force being applied to the operation end and outputs the operational information, a slave unit including an action part that applies an action to an object, and an operation part that moves the action part, and a control device. The control device includes a first determinator that determines a first coordinate system relationship that is a relationship between a slave coordinate system set to the slave unit and an object coordinate system set to the object, a second determinator that determines a second coordinate system relationship that is a relationship between a master coordinate system set to the master unit and the object coordinate system, and an operational commander that outputs an operational command for causing the operation part to operate the action part, according to the operational information, the first coordinate system relationship, and the second coordinate system relationship. When the object coordinate system is moved, the first determinator newly determines the first coordinate system relationship after the movement based on the moved object coordinate system and the slave coordinate system. When the object coordinate system is moved, the second determinator determines the second coordinate system relationship after the movement between the moved object coordinate system and the master coordinate system, as a relationship similar to the second coordinate system relationship before the movement.

According to the technique of the present disclosure, the master unit can be operated easily even when a target to which the slave unit applies an action is changed.

MODES FOR CARRYING OUT THE DISCLOSURE

Figure 1:
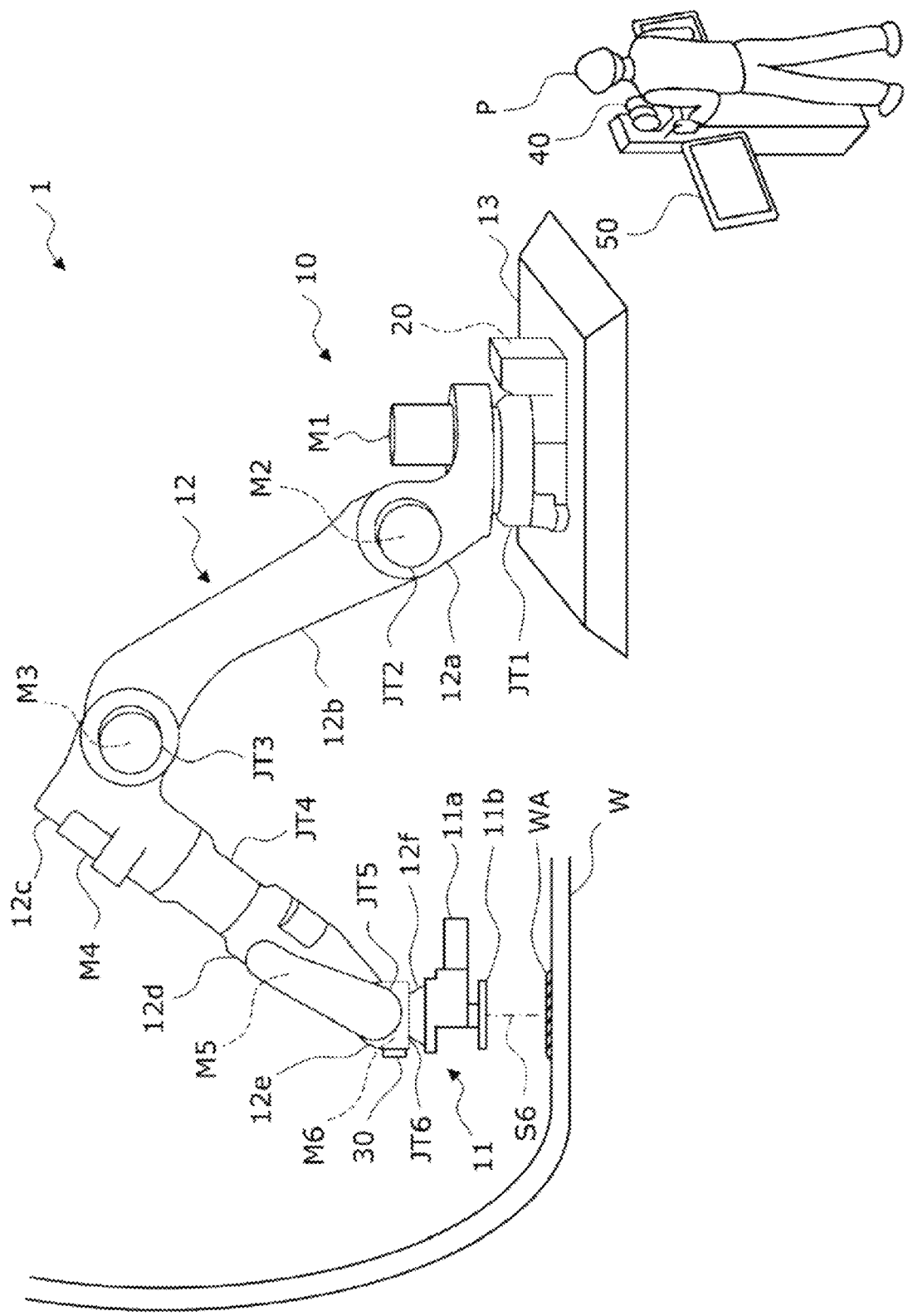
FIG. 1 is a schematic view illustrating one example of a robot system according to one embodiment.

First, one example of an embodiment of the present disclosure is described. A master-slave system according to one aspect of the present disclosure includes a master unit including an operation end, and an operation detector that detects operational information that is information inputted by a force being applied to the operation end and outputs the operational information, a slave unit including an action part that applies an action to an object, and an operation part that moves the action part, and a control device. The control device includes a first determinator that determines a first coordinate system relationship that is a relationship between a slave coordinate system set to the slave unit and an object coordinate system set to the object, a second determinator that determines a second coordinate system relationship that is a relationship between a master coordinate system set to the master unit and the object coordinate system, and an operational commander that outputs the operational command for causing the operation part to operate the action part, according to the operational information, the first coordinate system relationship, and the second coordinate system relationship. When the object coordinate system is moved, the first determinator newly determines the first coordinate system relationship after the movement based on the moved object coordinate system and the slave coordinate system. When the object coordinate system is moved, the second determinator determines the second coordinate system relationship after the movement between the moved object coordinate system and the master coordinate system, as a relationship similar to the second coordinate system relationship before the movement.

According to this aspect, when the object coordinate system is moved by a factor such that the position of the object changes, since the relative position of the slave unit and the object changes, the control device changes the first coordinate system relationship between the slave coordinate system and the object coordinate system. Meanwhile, the control device maintains the second coordinate system relationship between the master coordinate system and the object coordinate system before the movement as it is. For example, suppose that, before the movement of the object coordinate system, in response to the operational information that the force is applied to the operation end in a first direction in the master coordinate system, the control device outputs the operational command to operate the action part in a second direction in the object coordinate system. In this case, after the movement, the control device outputs the operational command to operate the action part in the second direction in the object coordinate system in response to the operational information that the force is applied to the operation end in the first direction in the master coordinate system. Thus, when the same manipulation is inputted between before and after the movement, the control device does not change the operation of the action part to the object coordinate system between before and after the movement. Therefore, when the object coordinate system is moved, an operator does not need to change the manipulation to input to the master unit according to the movement of the object coordinate system. According to this, the operation of the master unit becomes easy even when the target to which the slave unit applies operation changes.

The master-slave system according to the aspect of the present disclosure may further include a distance detecting device that detects an object distance that is a distance to the object. The control device may further include a coordinate system determinator that determines the object coordinate system based on the object distance detected by the distance detecting device. According to this aspect, when the object coordinate system is moved, the control device can determine by itself the moved object coordinate system based on the detection result of the distance detecting device.

In the master-slave system according to the aspect of the present disclosure, the distance detecting device may detect the object distance at a given time interval. The coordinate system determinator may determine to change the object coordinate system corresponding to the detected object distance. According to this aspect, the control device can change the object coordinate system based on the object distance detected at the given time interval by the distance detecting device. For example, the control device can change the object coordinate system corresponding to the state of the object on real time.

In the master-slave system according to the aspect of the present disclosure, the distance detecting device may detect the object distance at a given timing. The coordinate system determinator may determine to change the object coordinate system corresponding to the detected object distance. According to this aspect, the control device can change the object coordinate system based on the object distance detected at the given timing by the distance detecting device. Thus, the processing amount of the control device can be reduced.

In the master-slave system according to the aspect of the present disclosure, the distance detecting device may be an imaging device capable of capturing an image from which a distance to a photographic subject is detected. The control device may further include an image processor that detects the object distance by image-processing the image of the object captured by the imaging device. According to this aspect, by image-processing the image of the object, the three-dimensional position at each position of the object can be detected. Therefore, the control device can determine the object coordinate system corresponding to the shape, the position, and the posture of the object.

In the master-slave system according to the aspect of the present disclosure, the movement of the object coordinate system may include movement of a position and a posture of the object coordinate system. According to this aspect, the control device can perform the processing corresponding to the movement of the position and the posture of the object coordinate system.

In the master-slave system according to the aspect of the present disclosure, the operation detector may detect a direction and a magnitude of a force applied to the operation end as the operational information. The operational commander may generate the operational command including the position and the posture of the action part, and an action force to the object. According to this aspect, the command of the direction and the magnitude of the force applied to the operation end can be converted into the command of the moving direction of the action part, the moving speed, and the action force in the moving direction. Therefore, the operator can control the operation of the action part by applying the force to the operation end.

In the master-slave system according to the aspect of the present disclosure, the operation detector may detect magnitudes of forces in directions of three axes and moments of forces on the three axes applied to the operation end, as the operational information. According to this aspect, the command of the magnitudes of the forces the three axes applied to the operation end can be converted into the command of the moving speed of the action part along the three axes and the action forces. The command of the moments of forces on the three axes applied to the operation end can be converted into the command of the rotational speeds and the rotating forces of the action part on the three axes. Therefore, the operator can control the position and the posture of the action part by applying the force to the operation end.

In the master-slave system according to the aspect of the present disclosure, the action part may include a grinding device, and the operation part may include a robotic arm. According to this aspect, the master-slave system makes the grinding work by the grinding device possible while changing the position and the posture of the grinding device using the robotic arm.

A controlling method according to another aspect of the present disclosure is a method of controlling a slave unit manipulated by a master unit. The method includes the steps of determining a first coordinate system relationship that is a relationship between an object coordinate system set to an object to be processed by the slave unit and a slave coordinate system set to the slave unit, determining a second coordinate system relationship that is a relationship between a master coordinate system set to the master unit and the object coordinate system, and outputting an operational command for causing the slave unit to operate with respect to the object, according to the operational information that is information inputted into the master unit by a force being applied to an operation end of the master unit, the first coordinate system relationship, and the second coordinate system relationship. When the object coordinate system is moved, the first coordinate system relationship after the movement is newly determined based on the moved object coordinate system and the slave coordinate system, and the second coordinate system relationship after the movement between the moved object coordinate system and the master coordinate system is determined as a relationship similar to the second coordinate system relationship before the movement. According to this aspect, similar effects to the master-slave system according to the one aspect of the present disclosure are achieved. For example, the controlling method may be implementable by the control device.

Embodiment

Hereinafter, one embodiment of the present disclosure is described with reference to the drawings. Note that this embodiment which will be described below illustrates a comprehensive or concrete example. Further, components which are not described in the independent claims indicating the top concept among components in the following embodiment are described as arbitrary components. Each figure in the accompanying drawings is a schematic figure, and is not necessarily illustrated exactly. In each drawing, the same reference characters are assigned to substantially the same components, and therefore, redundant explanation may be omitted or simplified. The term "device" as used in this specification and the claims may not only mean a sole device, but may also mean a system comprised of a plurality of devices.

[Configuration of Robot System]

A configuration of a robot system 1 according to this embodiment is described. FIG. 1 is a schematic view illustrating one example of the robot system 1 according to this embodiment. As illustrated in FIG. 1, the robot system 1 according to this embodiment includes a robot 10, a control device 20, an imaging device 30, an operation input device 40, and a presentation device 50. The robot system 1 constitutes a master-slave system, where the robot 10 constitutes a slave unit, and the operation input device 40 constitutes a master unit. The control device 20 controls operation of the entire robot system 1. The control device 20 performs a bilateral control between the robot 10 and the operation input device 40.

In this embodiment, the robot 10 is an industrial robot. Although the robot 10 is fixedly disposed on a pedestal 13, it may be disposed on a movable device, such as a conveying device, so that it is movable. The robot 10 includes an end effector 11, as an action part, which applies an action to an object to be processed, and a robotic arm 12, as an operation part, which moves the end effector 11 to perform the action. In this embodiment, the following explanation is given as the end effector 11 applying the action, such as grinding, to the object. Such an end effector 11 is provided with a grinding device 11a which grinds the object, and it is attached to a tip end of the robotic arm 12. Note that the action of the end effector 11 is not limited to grinding, but may be any kind of action. For example, the action of the end effector 11 may be an action in which at least one of the position and the posture of the target of the action changes with progress of the action.

In this specification and the claims, "grinding" may include cutting which is machining for making the object into a required size, shape, etc. by removing unnecessary parts of the object, grinding which is machining for making the object into a required size, shape, surface roughness, etc. by shaving off the surface of the object, and polishing which is machining for smoothening the surface of the object.

Although the example of the grinding device 11a includes grinding devices which use electric power or air pressure as a power source, such as a grinder, an orbital sander, a random orbit sander, a delta sander, and a belt sander, it is not limited to these. The grinder may be a grinder which rotates a disk-shape grindstone, a grinder which rotates a cone- or pillar-shaped grindstone, etc.

In this embodiment, the following explanation is given such that the "grinding" is machining in which an unnecessary part in a grinding target area WA of a metal object W is shaved off to smoothen the surface of the grinding target area WA, and the grinding device 11a is an electric disk grinder provided with a disc-like grindstone 11b. The example of the unnecessary part in the grinding target area WA includes a welding mark, such as welding beads of the object W. The grinding device 11a grinds the welding mark and its vicinity by pressing the rotating grindstone 11b against the welding mark etc. in the grinding target area WA. The object W illustrated in FIG. 1 is a wall of a large-sized tank.

If the robotic arm 12 is changeable in the position and/or the posture of the grinding device 11a at a tip end thereof, the robotic arm 12 is, but not limited in particular to, a vertical articulated robotic arm in this embodiment. Note that the robotic arm 12 may be constituted as a robotic arm of a horizontal articulated type, a polar coordinate type, a cylindrical coordinate type, a Cartesian coordinate type, or other types.

The robotic arm 12 is fixed to the pedestal 13. The robotic arm 12 includes links 12a, 12b, 12c, 12d, and 12f which are serially disposed from its base part to its tip end, joints JT1, JT2, JT3, JT4, JT5, and JT6 which sequentially and pivotably connect the links 12a, 12b, 12c, 12d, and 12f, and arm drives M1, M2, M3, M4, M5, and M6 which rotate the respective joints JT1, JT2, JT3, JT4, JT5, and JT6. The link 12a is attached to the pedestal 13 via the joint JT1. A tip-end part of the link 12f constitutes a mechanical interface, which is connected to the end effector 11. The operations of the arm drives M1, M2, M3, M4, M5, and M6 are controlled by the control device 20. Although each of the arm drives M1, M2, M3, M4, M5, and M6 uses electric power as a power source, and has a servomotor Ma (see FIG. 4) as an electric motor which drives the arm drive, it is not limited to this configuration. Note that the number of joints of the robotic arm 12 is not limited to six, but it may be seven or more, or five or less.

Figure 2:
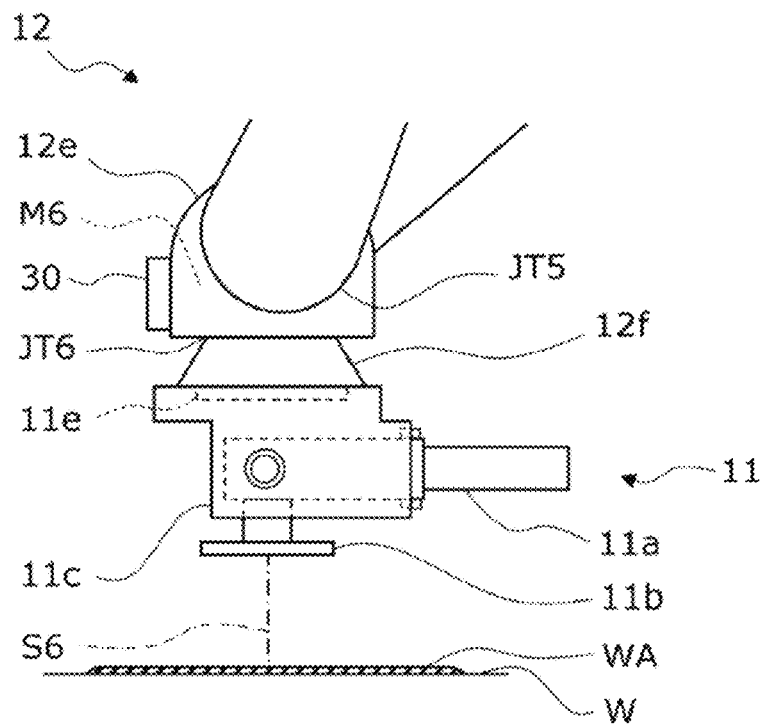
FIG. 2 is a side view illustrating one example of a configuration of an end effector according to this embodiment.

FIG. 2 is a side view illustrating one example of a configuration of the end effector 11 according to this embodiment. As illustrated in FIG. 2, the end effector 11 includes the grinding device 11a, a grindstone 11b, a fixture 11c, and a force sensor 11e. The fixture 11c supports the grinding device 11a, and it is connected to the link 12f so that the grinding device 11a is attached to the link 12f. The force sensor 11e is disposed between the fixture 11c and the link 12f. The force sensor 11e detects a reaction force which is a force acting on the link 12*f* from the fixture 11*c*, and outputs it to the control device 20. The reaction force is a force which the grinding device 11*a* receives from the object W during a grinding work. In this embodiment, although the force sensor 11*e* detects forces on six axes comprised of forces along three axes which are perpendicular to each other, and moments which are rotational forces on the three axes, it is not limited to this configuration, but it may detect only force(s) along one axis, two axes, or three axes, for example. For example, one of the three axes may be the same as a twist axis S6 of the link 12*f*.

As illustrated in FIGS. 1 and 2, the imaging device 30 is disposed at the link 12*e* of the robotic arm 12. The imaging device 30 may be provided with a camera (not illustrated), and may be further provided with a light source, such as an LED (light emitting diode) for illuminating a photographic subject, and a stroboscope. The camera of the imaging device 30 may be oriented in a direction along the axial direction of the twist axis S6 and toward the end effector 11 so that it images the grinding target area WA and its vicinity. Note that the position of the imaging device 30 may be any position as long as the grinding target area WA can be imaged, and it may be a position on the robotic arm 12 other than the link 12*e*, or a position exterior of the robotic arm 12. The imaging device 30 causes the camera to carry out an imaging operation in accordance with a command of the control device 20. The imaging device 30 sends a signal etc. of the image captured by the camera to the control device 20. Note that, in the following explanation, "imaging by the camera" may be expressed as "imaging by the imaging device 30."

The camera of the imaging device 30 images an image for detecting a three-dimensional position which is a position of a photographic subject in a three-dimensional space with respect to the imaging device 30, such as a distance to the photographic subject. For example, the camera images a digital image, which may be a stereo camera, a monocular camera, a TOF camera (Time-of-Flight-Camera), a pattern light projection camera of striped projection etc., or a camera using a light-section method. In this embodiment, the camera of the imaging device 30 is the stereo camera. The imaging device 30 is one example of a distance detecting device.

Figure 3:
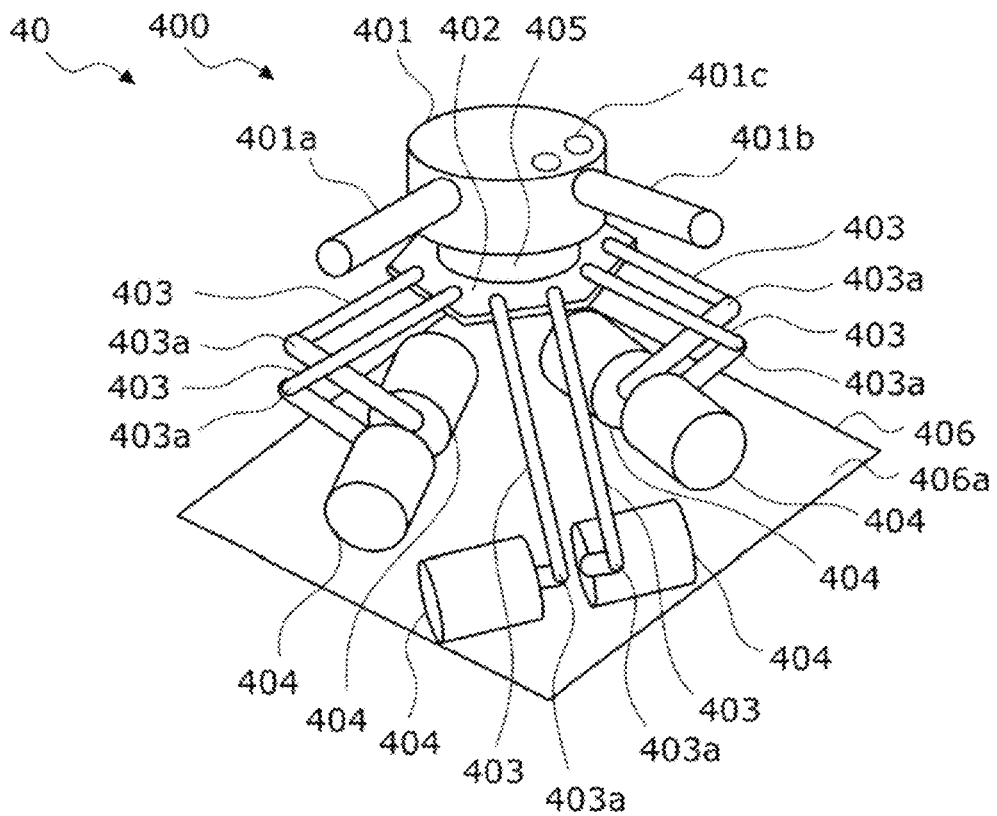
FIG. 3 is a perspective view illustrating one example of a configuration of a user interface of an operation input device according to this embodiment.
Figure 4:
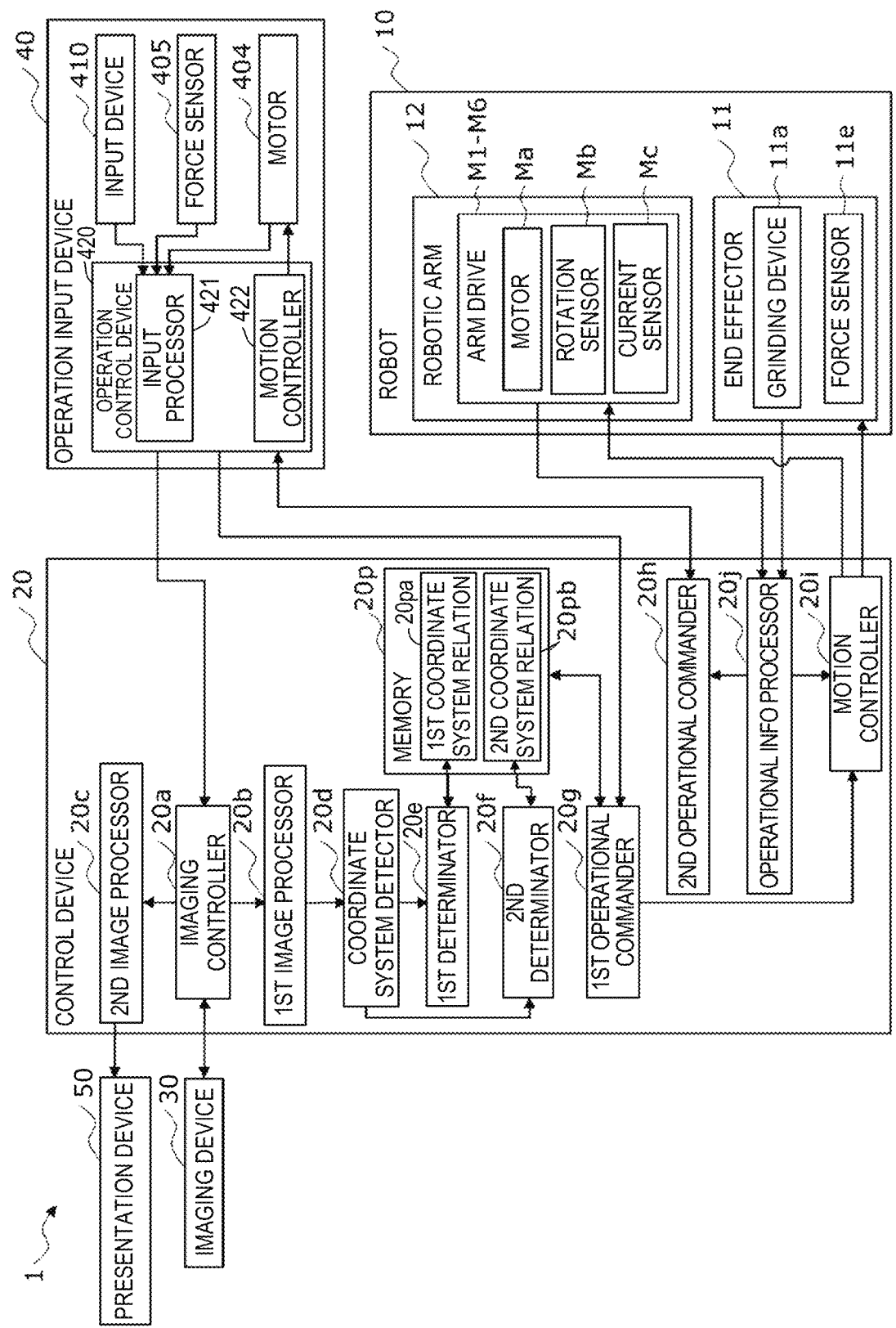
FIG. 4 is a block diagram illustrating one example of a functional configuration of the robot system according to this embodiment.

FIG. 3 is a perspective view illustrating one example of a configuration of a user interface 400 of the operation input device 40 according to this embodiment. FIG. 4 is a block diagram illustrating one example of a functional configuration of the robot system 1 according to this embodiment. As illustrated in FIGS. 1, 3, and 4, the operation input device 40 is disposed away from the robot 10, accepts an input, such as a command, data, and information, by a user P who manages and/or operates the robot system 1, and outputs the command, the data, the information, etc. to the control device 20. The operation input device 40 is connected with the control device 20 wiredly or wirelessly. The wired and wireless communications may be any kind of forms.

The operation input device 40 includes the user interface 400, an input device 410, and an operation control device 420. The operation control device 420 controls operation of the entire operation input device 40, and communicates the information, the command, the data, etc. with the control device 20. The user interface 400 accepts an input for manually operating the robot 10, and outputs operational information which is the inputted information to the operation control device 420. The user interface 400 gives, by a control of the operation control device 420, a reaction force against an operating force, to the user P who operates the user interface 400. The input device 410 accepts the input of the information, the command, the data, etc., and outputs it to the operation control device 420. For example, the input device 410 may be provided with a known input device, such as a lever, a button, a key, a touch panel, a joystick, and a motion capture. The input device 410 accepts an input, such as operation of the imaging device 30, switching of a control mode, information on the object to be ground, information on the grinding target area, etc. The information on the grinding target area may include information, such as the quantity, the position, the posture, the shape, and the size of the grinding target area.

As illustrated in FIG. 3, the user interface 400 includes a gripper 401, a support 402, arms 403, motors 404, and a force sensor 405. The gripper 401 is grippable by the user P. In this embodiment, although the gripper 401 has the same shape as the grinder which is the grinding device 11*a*, it is not limited to this configuration. The gripper 401 includes two handles 401*a* and 401*b* where the user P can grip. The user P grips the handles 401*a* and 401*b* like he/she grips the grinding device 11*a* and actually performs grinding, and moves the gripper 401 to operate the robot 10 so that the robot 10 performs a grinding operation. The gripper 401 includes an input part 401*c*, such as a push button, for operating the grinding device 11*a*. The gripper 401 is one example of an operation end.

The support 402 supports the gripper 401. The force sensor 405 is disposed between the gripper 401 and the support 402, and detects a force acting therebetween. In detail, the force sensor 405 detects forces of six axes comprised of forces along three axes perpendicular to each other, and moments which are rotational forces on the three axes. For example, one of the three axes may be an axis extending from the gripper 401 toward the support 402. The force sensor 405 is one example of an operation detector.

The support 402 is movably supported by the six arms 403. The six arms 403 are comprised of three pairs. The three pairs of arms 403 extend radiately in three directions from the support 402. Each arm 403 has a joint 403*a*, and is bendable centering on the joint 403*a*. One end of each arm 403 is connected with the support 402 via a universal joint, such as a ball joint, so as to be rotatable on the three axes perpendicular to each other. The other end of each arm 403 is connected, via a reduction gear (not illustrated) etc., with the rotation shaft of the motor 404 disposed on a surface 406*a* of a support table 406 below the support 402. The joint 403*a* of each arm 403 connects two columnar members which constitute the arm 403, via a universal joint, such as a ball joint, so as to be rotatable on the three axes perpendicular to each other.

The six motors 404 are disposed on the support table 406. The six motors 404 are comprised of three pairs. Each pair of motors 404 are disposed so that the rotation axes become coaxial, and are connected to one pair of arms 403. The three pairs of motors 404 are disposed so that their rotation axes constitute respective triangular sides. Each motor 404 is comprised of a servomotor etc.

The gripper 401 described above can take various positions and postures in the three-dimensional space. Corresponding to the position and the posture of the gripper 401, the arms 403 operate to rotate the respective motors 404. The rotating amounts of the six motors 404 corresponding to the position and the posture of the gripper 401 (i.e., a rotation angle) can be defined uniquely.

In this embodiment, the control device 20 performs a force orientation control by a bilateral method so that the position, the posture, and the force state correspond between the user interface 400 and the robot 10. Although not limited to this configuration, each motor 404 is provided with a rotation sensor (not illustrated), such as an encoder, which detects a rotation amount of a rotator of the servomotor, and a current sensor (not illustrated) which detects driving current of the servomotor. The operation control device 420 outputs operational information including detection signals of the forces of the six axes of the force sensor 405 (hereinafter, may also be referred to as the "force signal") to the control device 20 as a manipulation command for instructing the position, the posture, and a moving speed and the force of the position and the posture. The control device 20 uses the detection signals of the rotation sensor and the current sensor of each motor 404 (hereinafter, may also be referred to as the "rotation signal" and the "current signal") as feedback information for causing the motor 404 to generate the reaction force against the operating force by the user P. Note that the control device 20 may use the command value of the current supplied to the servomotor from a drive circuit of this servomotor, as feedback information. The manipulation command is one example of operational information.

The control device 20 generates an operational command (described later) using the manipulation command. The operational command includes commands for a three-dimensional position and the posture of the end effector 11, the moving speed of the position and the posture, and a force applied to the end effector 11, according to the manipulation command. Further, the control device 20 controls an output torque of each motor 404 based on force data of the six axes indicated by the detection signal of the force sensor 11e of the end effector 11, and the feedback information of the user interface 400. That is, the control device 20 servo-controls the six motors 404. The control device 20 controls the output torque of each motor 404 to generate a reaction force corresponding to the force data described above, in response to the operating force of the gripper 401 by the user P.

The configuration of the user interface 400 is not limited to the configuration of FIG. 3, but, for example, it may have such a configuration that, when operation to apply a force to a specific part by the user P is performed, it detects the operational information on this operation. For example, in the user interface 400, the gripper 401 may be fixed, a force applied to the gripper 401 may be detected by the force sensor 405, and the force signal of the force sensor 405 may be detected as the operational information. Alternatively, in the user interface 400, the moving amounts of the position and the posture of the gripper 401 which is moved by a force being applied may be detected as the operational information. The moving amount may be detected based on the rotation amount of each motor 404. Further, the force applied to the gripper 401 may be detected based on load of each motor 404 as the operational information. Alternatively, the user interface 400 may be comprised of a master robot similar to the robotic arm 12, and the robot 10 may be controlled as a slave robot. Alternatively, the user interface 400 may be a joystick.

The presentation device 50 presents to the user P of the robot system 1 an image, sound, etc. for operating the robot system 1 which is received from the control device 20. Although the example of the presentation device 50 includes a liquid crystal display, and an organic or inorganic EL (Electro Luminescence) display, it is not limited to these displays. The presentation device 50 may be provided with a speaker which outputs sound. For example, the presentation device 50 presents to the user P who operates the operation input device 40 the image captured by the imaging device 30.

[Hardware Configuration of Control Device]

Figure 5:
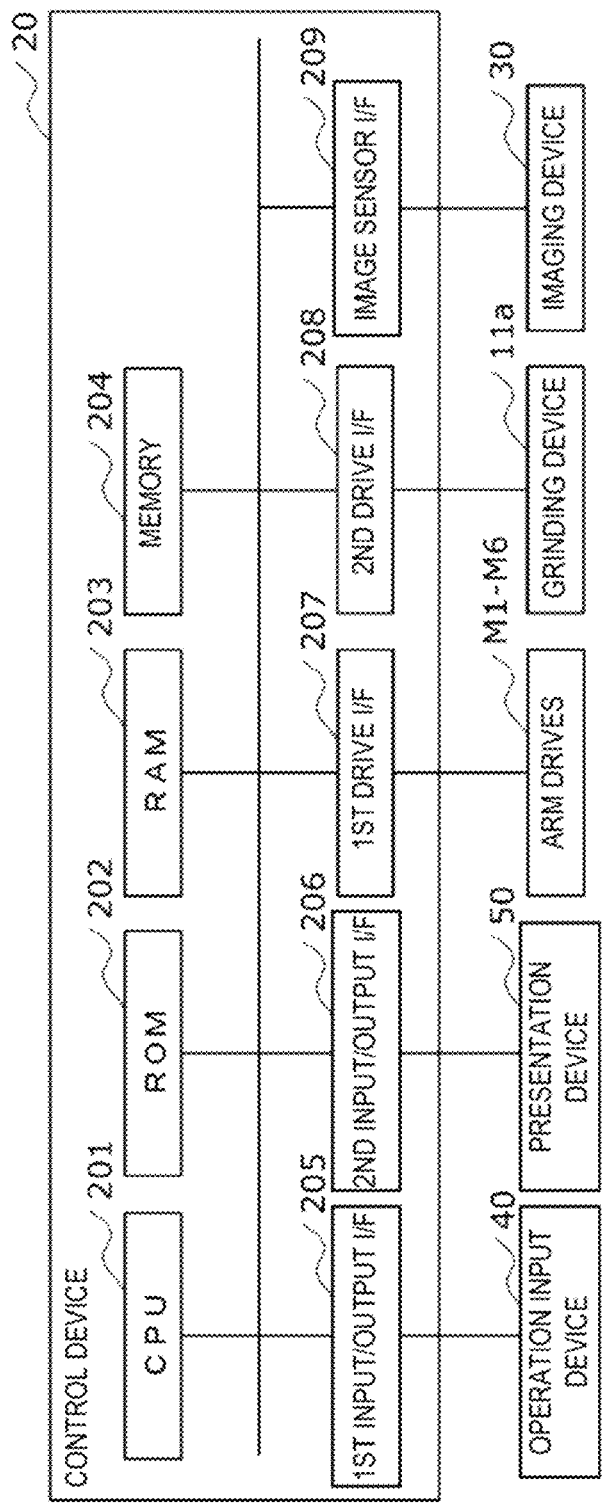
FIG. 5 is a block diagram illustrating one example of a hardware configuration of a control device according to this embodiment.

A hardware configuration of the control device 20 is described. FIG. 5 is a block diagram illustrating one example of the hardware configuration of the control device 20 according to this embodiment. As illustrated in FIG. 5, the control device 20 includes a CPU (Central Processing Unit) 201, a ROM (Read Only Memory) 202, a RAM (Random Access Memory) 203, a memory 204, input/output I/Fs (interfaces) 205 and 206, drive I/Fs 207 and 208, and an image sensor I/F 209, as components. The components described above are connected with each other via a bus, wiredly, or wirelessly. Not all the components described above are essential.

For example, the CPU 201 is a processor, which controls entire operation of the control device 20. The ROM 202 is comprised of a nonvolatile semiconductor the memory, which stores a program, data, etc. for causing the CPU 201 to control the operation. The RAM 203 is comprised of a volatile semiconductor memory, which temporarily stores the program to be executed by the CPU 201, and processing or processed data. The memory 204 is comprised of a storage device, such as a semiconductor memory such as a volatile memory and a nonvolatile memory, a hard disk drive (HDD), and an SSD (Solid State Drive), which stores various information.

For example, the program for operating the CPU 201 is saved beforehand in the ROM 202 or the memory 204. The CPU 201 reads the program from the ROM 202 or the memory 204, and develops it to the RAM 203. The CPU 201 executes each coded command in the program developed in the RAM 203.

Each function of the control device 20 may be realized by a computer system comprised of the CPU 201, the ROM 202, and the RAM 203, or may be realized by hardware circuitry for exclusive use, such as an electronic circuit or an integrated circuit, or may be realized by a combination of the computer system and the hardware circuitry.

Such a control device 20 may be comprised of, for example, a microcontroller, an MPU (Micro Processing Unit), an LSI (Large Scale Integration), a system LSI, a PLC (Programmable Logic Controller), or a logical circuit. A plurality of functions of the control device 20 may be realized by respective chips, or may be realized by a single chip so as to include a part or all of the functions. Further, the circuitry may be general-purpose circuitry, or may be circuitry for exclusive use. As the LSI, an FPGA (Field Programmable Gate Array) which is programmable after the LSI production, a reconfigurable processor which is reconfigurable of the connection and/or the setup of circuit cells inside the LSI, or an ASIC (Application Specific Integrated Circuit) by which circuits for a plurality of functions are assembled in one circuit for the particular application, may be used.

The image sensor I/F 209 controls the drive of an image sensor (not illustrated) of the camera of the imaging device 30 according to the command of the CPU 201. The image sensor I/F 209 takes into the RAM 203 or the memory 204 a signal of the image captured by the imaging device 30. Inside or outside of the control device 20, a circuit etc. for the drive of the imaging device 30 may be provided between the image sensor I/F 209 and the imaging device 30.

The first input/output I/F 205 is connected to the operation input device 40, and communicates signals, such as information, data, and a command. A circuit etc. for converting and amplifying a signal may be provided between the first input/output I/F 205 and the operation input device 40, inside or outside of the control device 20.

The second input/output I/F 206 is connected to the presentation device 50, and communicates signals, such as image data, sound data, information, and a command. A circuit etc. for converting and amplifying a signal may be provided between the second input/output I/F 206 and the presentation device 50, inside or outside of the control device 20.

The first drive I/F 207 is connected to the arm drives M1, M2, M3, M4, M5, and M6 of the robot 10, and communicates signals, such as information and a command. An arm drive circuit (not illustrated) is provided between the first drive I/F 207 and the arm drives M1, M2, M3, M4, M5, and M6, inside or outside of the control device 20. The arm drive circuit supplies electric power to servomotors Ma of the arm drives M1, M2, M3, M4, M5, and M6 according to the command of the CPU 201 to control the drive of each servomotor Ma.

The second drive I/F 208 is connected to the grinding device 11a of the end effector 11, and communicates signals, such as information and a command. A grinding drive circuit (not illustrated) is provided between the second drive I/F 208 and the grinding device Ha, inside or outside of the control device 20. The grinding drive circuit supplies electric power to the grinding device 11a according to the command of the CPU 201 to control the drive of the grinding device 11a.

[Functional Configuration of Robot System]

A functional configuration of the robot system 1 is described. As illustrated in FIG. 4, the operation control device 420 of the operation input device 40 includes an input processor 421 and a motion controller 422, as functional components. The control device 20 includes an imaging controller 20a, image processors 20b and 20c, a coordinate system detector 20d, determinators 20e and 20f, operational commanders 20g and 20h, a motion controller 20i, an operational information processor 20j, and a memory 20p, as functional components. Not all the functional components described above are essential.

The functions of the input processor 421 and the motion controller 422 of the operation control device 420 are realized by a computer system such as a CPU, hardware circuitry, or a combination of the computer system and the hardware circuitry. The functions of the functional components of the control device 20, except for the memory 20p, are realized by the CPU 201 etc., and the function of the memory 20p is realized by the memory 204, the ROM 202, and/or the RAM 203.

The input processor 421 of the operation control device 420 outputs to the control device 20 information, data, a command, etc. received from the input device 410, the force sensor 405, and the motor 404. For example, the input processor 421 receives a command of operation of the imaging device 30, a command of a change in the object coordinate system, a command of a change in a control mode, information on an object to be ground, and information on a grinding target area from the input device 410. The command of operation of the imaging device 30 includes commands, such as a start of imaging, an end of imaging, and a timing of imaging. The command of a change in the object coordinate system includes a command for changing the object coordinate system which is a coordinate system set as the target area of grinding, and a command for resuming the changed object coordinate system. The command of a change in the control mode includes a command for changing between a control mode in which the object coordinate system is changed automatically and a control mode in which it is not changed automatically.

The input processor 421 detects the detection values of the forces of the six axes from the force signals of the force sensor 405. The input processor 421 outputs the detection values of the forces of the six axes, or processed values of the detection values of the forces of the six axes to the control device 20. For example, the input processor 421 processes the detection values of the forces of the six axes to generate a manipulation command to the end effector 11, and outputs it to the control device 20. The manipulation command includes a manipulational position command for instructing a change amount, a change direction, a rate of change in the position of the end effector 11, and a change amount, a change direction, and a rate of change in the posture of the end effector 11, and a manipulational force command for instructing a magnitude and a direction of the action force which the end effector 11 applies to the object.

The input processor 421 receives the detection signals of the rotation sensor and the current sensor from each motor 404, detects the rotation amount and the current value of the motor 404 based on the detection signals, and outputs them to the control device 20 as feedback information.

The motion controller 422 controls the drive of each motor 404 according to a motor operational command received from the second operational commander 20h of the control device 20. The motion controller 422 causes each motor 404 to generate rotational load (may also be referred to as the "load torque") according to the operational command described above. This rotational load acts as a reaction force to the operating force which the user P gives to the gripper 401 of the user interface 400. Therefore, the user P can operate the gripper 401, while sensing the reaction force from the gripper 401, for example, as if he/she receives the reaction force from the object.

The memory 20p of the control device 20 stores various information, and allows a read-out of the information stored therein. For example, the memory 20p stores information inputted via the input device 410 of the operation input device 40. Further, the memory 20p stores, as information used for image processing, camera parameters including external parameters and internal parameters of the camera of the imaging device 30. The example of the external parameter includes parameters indicative of the position (three-dimensional position) and the orientation (a direction of the optical axis) of the camera. The example of the internal parameter includes parameters indicative of a distortion, a focal length, a size of each pixel of an image sensor, pixel coordinates of the optical axis of a lens of the camera. The memory 20p may store the object to be ground by the robot 10, and a position, a shape, a size, etc. of the grinding target area of the object in association with each other. Alternatively, the memory 20p may store the image data captured by the imaging device 30, processed image data of the image data, and/or the program.

Further, the memory 20p stores a first coordinate system relationship 20pa and a second coordinate system relationship 20pb. The first coordinate system relationship 20pa is a relationship between a robot coordinate system Cr set to the robot 10, and an object coordinate system Cw set to the object. The second coordinate system relationship 20pb is a relationship between a manipulation coordinate system Cc set to the user interface 400, and the object coordinate system Cw. Note that the memory 20p may also store the robot coordinate system Cr, the manipulation coordinate system Cc, and the object coordinate system Cw. The robot coordinate system Cr is one example of a slave coordinate system, and the manipulation coordinate system Cc is one example of a master coordinate system.

Figure 6:
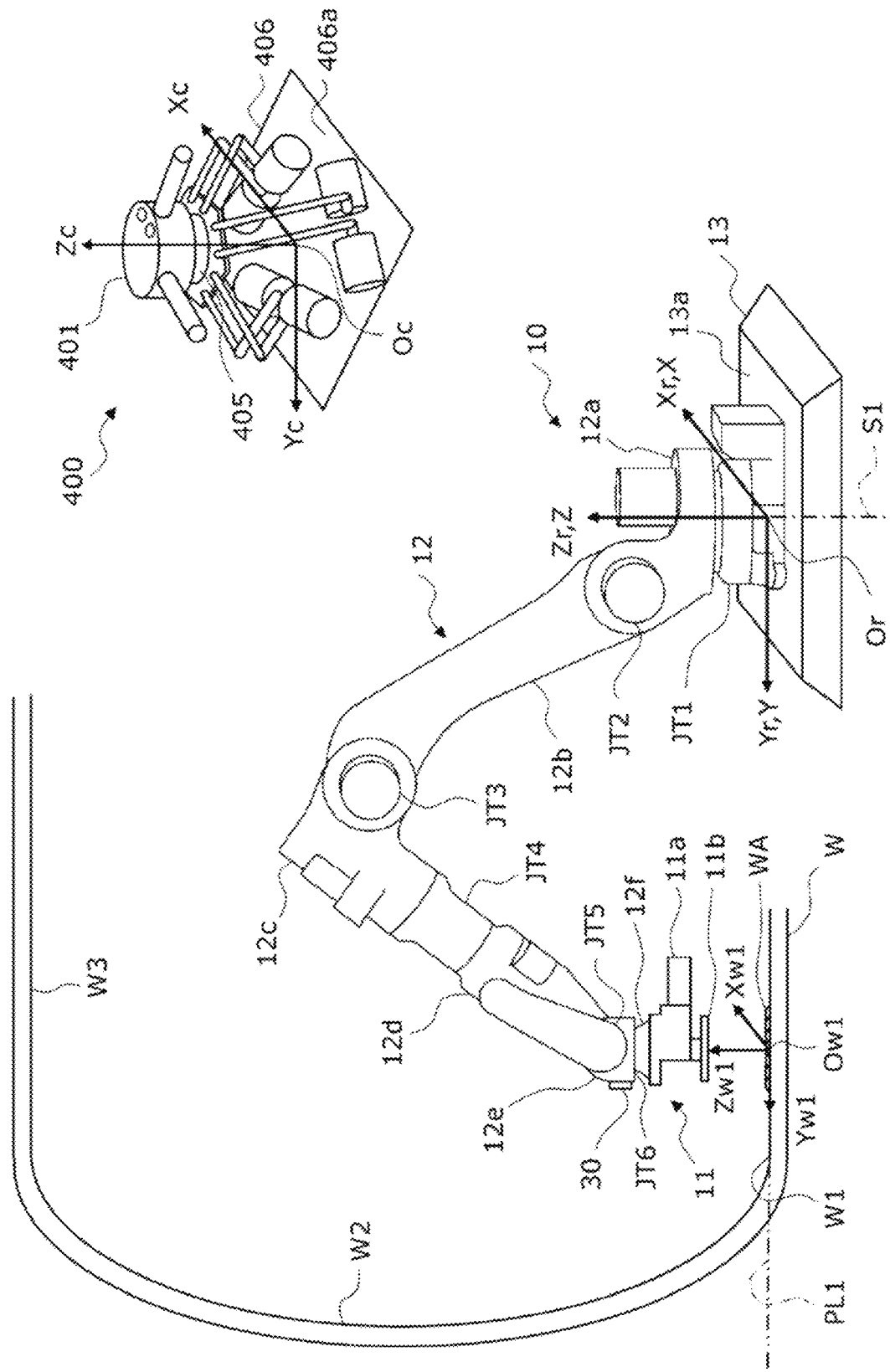
FIG. 6 is a view illustrating one example of each coordinate system in the robot system of FIG. 1.

Here, each coordinate system is described. FIG. 6 is a view illustrating one example of each coordinate system in the robot system 1 of FIG. 1. As illustrated in FIG. 6, the robot coordinate system Cr is a coordinate system on the basis of the robot 10. In this embodiment, the robot coordinate system Cr is a coordinate system on the basis of the pedestal 13 where the robotic arm 12 is installed. Xr-axis, Yr-axis, and Zr-axis are defined in the robot coordinate system Cr. For example, the Xr-axis and the Yr-axis extend along a surface 13a of the pedestal 13, and are perpendicular to each other. The Zr-axis extends perpendicular to the Xr-axis and the Yr-axis (that is, perpendicular to the surface 13a). For example, an origin Or of the robot coordinate system Cr is an intersection of the rotation center axis S1 of the joint JT1 and the surface 13a. A direction which goes upward from the surface 13a is the positive direction in the Zr-axis, and the opposite direction is the negative direction in the Zr-axis. The position of the origin Or of the robot coordinate system Cr, and directional vectors of the Xr-axis, the Yr-axis, and the Zr-axis are defined using the world coordinate system.

Although not limited to this configuration, in this embodiment, the X-axis, the Y-axis, and the Z-axis of the world coordinate system set to the space where the robot 10 is disposed are the same as the Xr-axis, the Yr-axis, and the Zr-axis of the robot coordinate system Cr, respectively.

The object coordinate system Cw is a coordinate system on the basis of a specific point and a specific plane of the object W. In this embodiment, the object coordinate system Cw uses a plane along the surface of the object W where the grinding target area WA exists, as a reference plane, and uses a specific point within the grinding target area WA as a reference point. In FIG. 6, a point Ow1 within the grinding target area WA on an inner surface W1 of the object W is the reference point, and a flat plane PL1 passing through the point Ow1 and parallel to the inner surface W1 is the reference plane. In the object coordinate system Cw, Xw-axis, Yw-axis, and Zw-axis are defined, and an object coordinate system Cw1 which is one of the object coordinate systems Cw, Xw1-axis, Yw1-axis, and Zw1-axis are defined. The Xw1-axis and the Yw1-axis are included in the flat plane PL1, and are perpendicular to each other at the point Ow1. The Zw1-axis is perpendicular to the Xw1-axis and the Yw1-axis at the point Ow1. A direction inward from the inner surface W1 is the positive direction of the Zw1-axis, and the opposite direction is the negative direction of the Zw1-axis. The position of an origin Ow of the object coordinate system Cw, and direction vectors of the Xw-axis, the Yw-axis, and the Zw-axis are defined using the world coordinate system.

The manipulation coordinate system Cc is a coordinate system on the basis of the user interface 400. In this embodiment, the manipulation coordinate system Cc uses a plane fixed to the user interface 400 as the reference plane, and uses a specific point on the reference plane as the reference point. In FIG. 6, the surface 406a of the support table 406 is the reference plane, and a specific point Oc on the surface 406a is the reference point. In the manipulation coordinate system Cc, Xc-axis, Yc-axis, and Zc-axis are defined. The Xc-axis and the Yc-axis are included in the surface 406a, and are perpendicular to each other at the point Oc. The Zc-axis is perpendicular to the Xc-axis and the Yc-axis at the point Oc. The direction toward the gripper 401 from the surface 406a is the positive direction of the Zc-axis, and the opposite direction is the negative direction of the Zc-axis. The manipulation coordinate system Cc may be or may not be associated with the world coordinate system.

The first coordinate system relationship 20pa is a relationship between the robot coordinate system Cr and the object coordinate system Cw. For example, the first coordinate system relationship 20pa may be a relationship of the positions and the postures between the robot coordinate system Cr and the object coordinate system Cw. For example, the relationship described above may be a relationship of the positions and the postures of the axes of coordinates. The relationship of the positions and the postures of the axes of coordinates may be a relationship of the positions and the postures between the Xr-axis, the Yr-axis, and the Zr-axis of the robot coordinate system Cr on the basis of the world coordinate system, and the Xw-axis, the Yw-axis, and the Zw-axis of the object coordinate system Cw. Alternatively, the relationship of the positions and the postures of the axes of coordinates may be a relationship of the positions and the postures between the Xr-axis, the Yr-axis, and the Zr-axis on the basis of the robot coordinate system, and the Xw-axis, the Yw-axis, and the Zw-axis.

For example, in FIG. 6, the first coordinate system relationship 20pa indicates that the Xr-axis and the Xw1-axis are parallel and are the same direction, and the Yr-axis and the Yw1-axis are parallel and are the same direction, and the Zr-axis and the Zw1-axis are parallel and are the same direction. The first coordinate system relationship 20pa also indicates a spatial relationship between the origin Or of the robot coordinate system Cr and the origin Ow1 of the object coordinate system Cw1. For example, when the robot 10 moves the end effector 11 in the positive direction of the Yr-axis, the end effector 11 moves in the positive direction of the Yw1-axis.

The second coordinate system relationship 20pb is a relationship between the manipulation coordinate system Cc and the object coordinate system Cw. For example, the second coordinate system relationship 20pb may be a correspondence relationship of coordinates between the manipulation coordinate system Cc and the object coordinate system Cw. The correspondence relationship of the coordinates may be a correspondence relationship of the axes of coordinates, such as a correspondence relationship between the Xc-axis, the Yc-axis, and the Zc-axis of the manipulation coordinate system Cc, and the Xw-axis, the Yw-axis, and the Zw-axis of the object coordinate system Cw, or may be a correspondence relationship of the coordinate points between the manipulation coordinate system Cc and the object coordinate system Cw. The example of the correspondence relationship of the axes of coordinates includes a relationship in which the Xc-axis corresponds to the Xw-axis, the Yc-axis corresponds to the Yw-axis, and the Zc-axis corresponds to the Zw-axis. Note that the Xc-axis, the Yc-axis, and the Zc-axis may correspond to the Xw-axis, the Yw-axis, and the Zw-axis which are different from the above, respectively, or may correspond to axes in the object coordinate system Cw other than the Xw-axis, the Yw-axis, and the Zw-axis. The example of the correspondence relationship of the coordinate points includes a relationship in which the coordinate points (Xck, Yck, and Zck) (k: an integer equal to or larger than 1) of the manipulation coordinate system Cc correspond to the coordinate points (Xwk, Ywk, and Zwk) of the object coordinate system Cw, respectively.

For example, in FIG. 6, the second coordinate system relationship 20pb indicates that the positive direction and the negative direction of the Xc-axis correspond to the positive direction and the negative direction of the Xw1-axis, the positive direction and the negative direction of the Yc-axis correspond to the positive direction and the negative direction of the Yw1-axis, and the positive direction and the negative direction of the Zc-axis correspond to the positive direction and the negative direction of the Zw1-axis, respectively. For example, the command for moving the gripper 401 in the positive direction of the Yc-axis is a command for moving the end effector 11 in the positive direction of the Yw1-axis.

The imaging controller 20a controls the operation of the imaging device 30 to acquire the image data captured by the imaging device 30. The imaging controller 20a associates with each other two image data captured at the same time by the imaging device 30 provided with the stereo camera, and outputs them to the image processors 20b and 20c etc. Capturing the image by the imaging device 30, and acquiring the image data captured by the imaging device 30 include acquiring one still image data captured by the imaging device 30, and acquiring still image data of one frame from video data imaged by the imaging device 30. For example, the imaging controller 20a causes the imaging device 30 to image at a given timing or a given time period. For example, the given timing may be a timing set beforehand, a timing specified by the user P via the operation input device 40, etc. For example, the timing set beforehand may be a temporal timing, a timing corresponding to the progress of grinding work, etc.

The first image processor 20b processes the image data acquired from the imaging controller 20a to detect the three-dimensional position of each position of the photographic subject projected onto the image data, and generate the three-dimensional image data which is the image data indicative of the three-dimensional position of each position. In detail, the first image processor 20b identifies the grinding target area WA of the object W projected onto each of the two image data captured at the same time by the imaging device 30. For example, the first image processor 20b may compare it by a pattern matching technique etc. with the shape of the grinding target area WA stored in the memory 20p to extract an edge of the grinding target area WA in each image data. Further, the first image processor 20b performs image processing by a stereo matching technique etc. using the camera parameters stored in the memory 20p to detect a distance between a photographic subject projected to at least three pixels and the imaging device 30, within the grinding target area WA of at least one of the two image data. Further, the first image processor 20b detects a three-dimensional position in the three-dimensional space where the robot system 1 exists, for the photographic subject projected onto each pixel from which the distance is detected. The first image processor 20b outputs the detection result to the coordinate system detector 20d.

The second image processor 20c outputs the image data acquired from the imaging controller 20a and displays it on the presentation device 50. The second image processor 20c may acquire the processed image data from the first image processor 20b, and may output the image data indicative of the three-dimensional shape of the grinding target area WA to the presentation device 50. For example, the image data described above may be a distance image of which a pixel value of each pixel is a distance value from the imaging device 30 to the photographic subject. The distance value may be expressed by the shade or color of the pixel.

Using the three-dimensional positions of at least three pixels of the grinding target area WA acquired from the first image processor 20b, the coordinate system detector 20d detects a new object coordinate system Cwd of the grinding target area WA, and outputs it to the determinators 20e and 20f. At this time, the coordinate system detector 20d detects, in the world coordinate system, the position of the origin Owd of the new object coordinate system Cwd, and the direction vectors of Xwd-axis, Ywd-axis, and Zwd-axis. The coordinate system detector 20d is one example of a coordinate system determinator.

In detail, the coordinate system detector 20d detects a plane formed in the three-dimensional space by the three-dimensional positions of the photographic subject projected onto at least three pixels, determines this plane as an Xwd-Ywd plane of the object coordinate system Cwd, and determines an axis vertical to the plane as the Zwd-axis. For example, the coordinate system detector 20d may determine an axis in the Xr-axis direction along the plane described above as the Xwd-axis, and may determine a direction in the positive direction of the Xr-axis as the positive direction of the Xwd-axis. Further, the coordinate system detector 20d may determine an axis in the Yr-axis direction along the above described plane as the Ywd-axis, and may determine a direction in the positive direction of the Yr-axis as the positive direction of the Ywd-axis. Further, for the Zwd-axis, the coordinate system detector 20d may determine a direction toward the pedestal 13 from the plane described above as the positive direction of the Zwd-axis.

Note that the method of detecting the plane may be any kind of known methods. For example, the coordinate system detector 20d may determine a plane passing through the three-dimensional positions of the photographic subject projected onto at least three pixels as the Xwd-Ywd plane. Alternatively, the coordinate system detector 20d may determine a plane passing through the three-dimensional positions of the photographic subject projected onto at least three pixels, or their vicinities (i.e., a plane which approximates to the at least three three-dimensional positions) as the Xwd-Ywd plane. Alternatively, for example, the coordinate system detector 20d detects a curved surface passing through the three-dimensional positions of the photographic subject projected onto at least three pixels, and may determine a plane which is vertical to the normal of the curved surface and has an intersection with the curved surface as the Xwd-Ywd plane. For example, in FIG. 7, the coordinate system detector 20d detects a plane passing through the three-dimensional positions of the photographic subject projected onto the three pixels, and determines a flat plane PL2 which comes in contact with an inner surface W2 of the object W in the Yr-axis direction which is the normal direction of the plane, as an Xw2-Yw2 plane. The inner surface W2 is a curved surface extending in the vertical direction. Note that FIG. 7 is a view illustrating one example of movement in each coordinate system of the robot system 1 of FIG. 6.

When the coordinate system detector 20d receives a command for changing the object coordinate system Cw via the operation input device 40, it determines the object coordinate system Cwd detected from the three-dimensional positions of at least three pixels acquired from the first image processor 20b as a new object coordinate system Cw, and outputs it to the determinators 20e and 20f.

Alternatively, the coordinate system detector 20d detects the object coordinate system Cwd from the three-dimensional positions of at least three pixels acquired from the first image processor 20b, in a control mode in which the object coordinate system Cw is changed automatically, and detects a difference between a current object coordinate system Cwp and the detected object coordinate system Cwd. When one or both of a condition that a difference in the position between origins Owd and Owp of the object coordinate systems Cwd and Cwp is above a first threshold, and a condition that a difference in the posture between the object coordinate systems Cwd and Cwp is above the second threshold, is satisfied, the coordinate system detector 20*d* determines the detected object coordinate system Cwd as the new object coordinate system, and outputs it to the determinators 20*e* and 20*f*. For example, the difference in the posture between the object coordinate systems Cwd and Cwp being above the second threshold may be one of, two of, or three of a difference in the direction angle between the Xwd-axis and Xwp-axis, a difference in the direction angle between the Ywd-axis and Ywp-axis, and a difference in the direction angle between the Zwd-axis and Zwp-axis, being above the second threshold.

Figure 7:
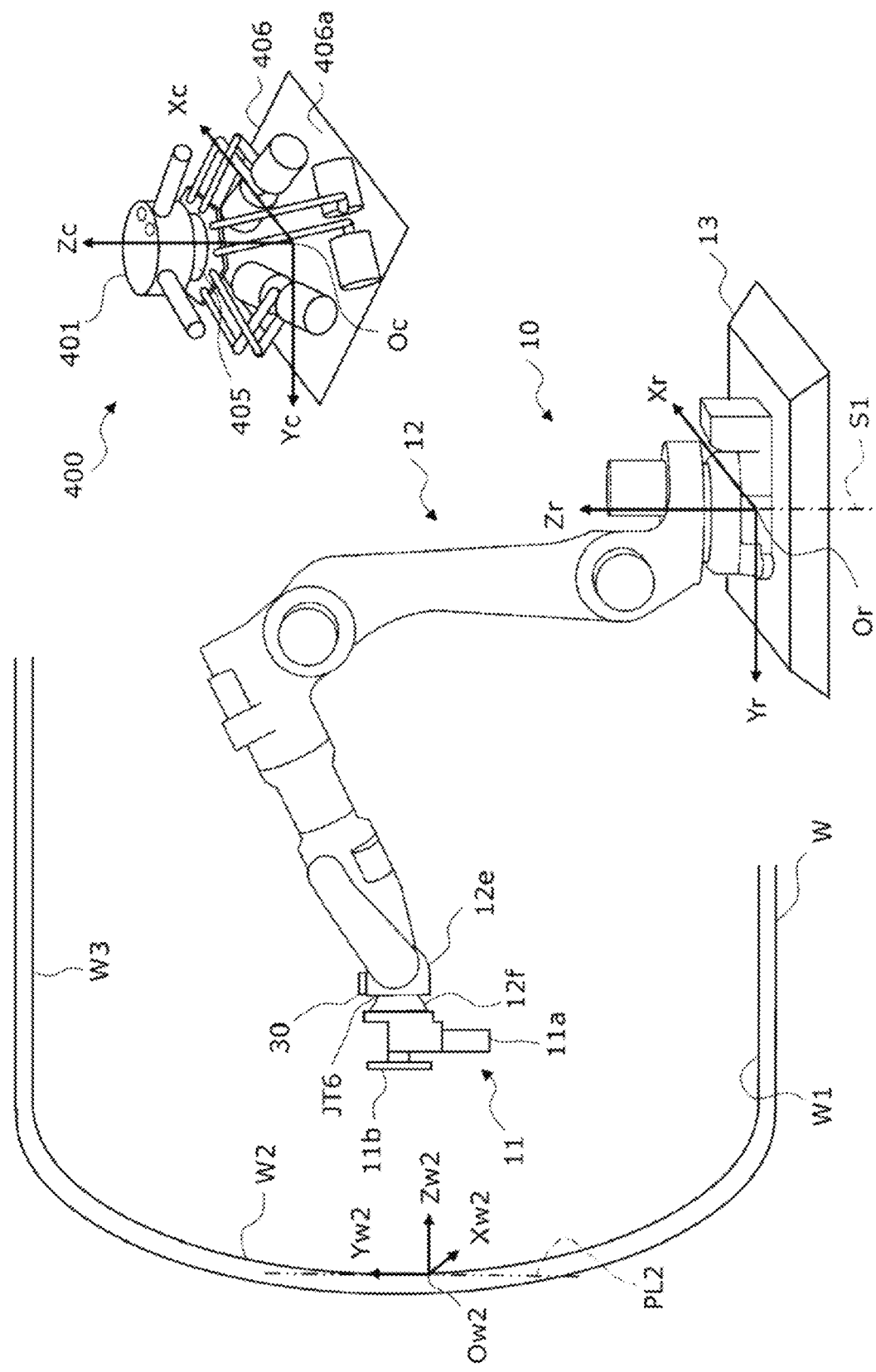
FIG. 7 is a view illustrating one example of movement in each coordinate system of the robot system of FIG. 6.
Figure 8:
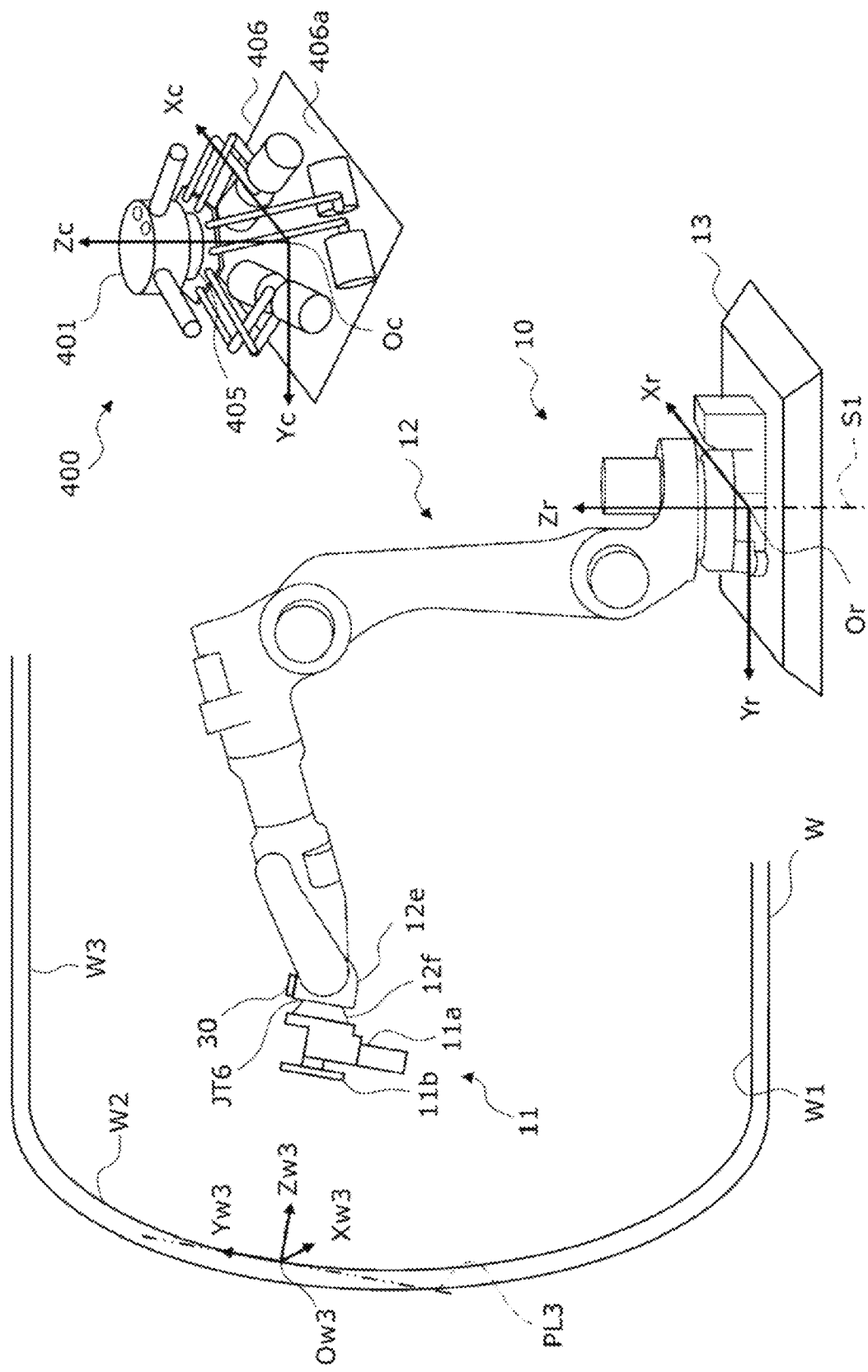
FIG. 8 is a view illustrating one example of movement in each coordinate system of the robot system of FIG. 6.

For example, as illustrated in FIGS. 7 and 8, when an object coordinate system Cw3 after the detection is comprised of Xw3 axis, Yw3 axis, and Zw3 axis against a current object coordinate system Cw2 comprised of Xw2-axis, Yw2-axis, and Zw2-axis of FIG. 7, a difference in the direction angle of the Yw-axis and the Zw-axis between the object coordinate systems Cw2 and Cw3 is above the second threshold. On the other hand, a difference in the positions of the origins Ow between the object coordinate systems Cw2 and Cw3 is below the first threshold. In this case, the coordinate system detector 20*d* determines the object coordinate system Cw3 as the new object coordinate system. Note that FIG. 8 is a view illustrating one example of movement in each coordinate system of the robot system 1 of FIG. 6.

The first determinator 20*e* determines a new first coordinate system relationship 20*pa* based on the detection result of the coordinate system detector 20*d*, and updates the first coordinate system relationship 20*pa* stored in the memory 20*p*. When the first determinator 20*e* receives the new object coordinate system Cwd from the coordinate system detector 20*d*, it determines the relationship between the new object coordinate system Cwd and the robot coordinate system Cr as the new first coordinate system relationship 20*pa*. For example, the first determinator 20*e* may determine the new first coordinate system relationship 20*pa* based on the relationship of the position and the posture between the new object coordinate system Cwd and the robot coordinate system Cr. For example, the first determinator 20*e* calculates an expression indicative of the new relationship between the new object coordinate system Cwd and the robot coordinate system Cr, and replaces the expression indicative of the current relationship between the current object coordinate system Cwp and the robot coordinate system Cr with the new expression. For example, the first determinator 20*e* calculates a function "M1*p*" using the current expression as "Cwp=M1*p*·Cr," and calculates a function "M1*d*" using the new expression as "Cwd=M1*d*·Cr," and replaces (i.e., updates) the expression. For example, the functions "M1*d*" and "M1*p*" may be functions for coordinate conversion in which the axis of coordinates is parallelly translated and rotated.

Therefore, when the object coordinate system Cwp is moved to the object coordinate system Cwd, the first determinator 20*e* determines the relationship between the moved object coordinate system Cwd and the robot coordinate system Cr as the new first coordinate system relationship 20*pa*. Note that moving the object coordinate system Cwp may be moving at least one of the position and the posture of the object coordinate system Cwp.

The second determinator 20*f* determines a new second coordinate system relationship 20*pb* based on the detection result of the coordinate system detector 20*d*, and updates the second coordinate system relationship 20*pb* stored in the memory 20*p*. When the new object coordinate system Cwd is received from the coordinate system detector 20*d*, the second determinator 20*f* determines the relationship between the new object coordinate system Cwd and the manipulation coordinate system Cc as the new second coordinate system relationship 20*pb*, assuming that it is a relationship similar to the relationship between the current object coordinate system Cwp and the manipulation coordinate system Cc. For example, the second new determinator 20*f* may determine a correspondence relationship of the axis of coordinates and/or the coordinate point between the new object coordinate system Cwd and the manipulation coordinate system Cc as the new second coordinate system relationship 20*pb*, assuming that it is a relationship similar to the correspondence relationship of the axis of coordinates and/or the coordinate point between the current object coordinate system Cwp and the manipulation coordinate system Cc. For example, the second determinator 20*f* uses the function "M2" stored in the memory 20*p* to define the current expression between the current object coordinate system Cwp and the manipulation coordinate system Cc as "Cwp=M2·Cc," defines the new expression between the new object coordinate system Cwd and the manipulation coordinate system Cc as "Cwd=M2·Cc," and replaces (i.e., updates) the expression. For example, the function "M2" may be a function for multiplying by a constant number in each axis-of-coordinates direction.

For example, in this embodiment, the movements in the positive direction of the Xc-axis, in the positive direction of the Yc-axis, and in the positive direction of the Zc-axis of the manipulation coordinate system Cc correspond to the movements in the positive direction of the Xwp-axis, in the positive direction of the Ywp-axis, and in the positive direction of the Zwp-axis of the object coordinate system Cwp, and the constant (Kt) multiples of the moving amounts in the positive direction of the Xc-axis, in the positive direction of the Yc-axis, and in the positive direction of the Zc-axis correspond to the moving amounts in the positive direction of the Xwp-axis, in the positive direction of the Ywp-axis, and in the positive direction of the Zwp-axis, respectively. Further, the rotations and the rotating directions on the Xc-axis, the Yc-axis, and the Zc-axis correspond to the rotations and the rotating directions on the Xwp-axis, the Ywp-axis, and the Zwp-axis, respectively, and the constant (Kr) multiples of the rotation amounts on the Xc-axis, the Yc-axis, and the Zc-axis correspond to the rotation amounts on the Xwp-axis, the Ywp-axis, and the Zwp-axis, respectively.

The movements in the positive direction of the Xc-axis, in the positive direction of the Yc-axis, and in the positive direction of the Zc-axis correspond to the movements in the positive direction of the Xwd-axis, in the positive direction of the Ywd-axis, and in the positive direction of the Zwd-axis of the object coordinate system Cwd, respectively, and the constant (Kt) multiples of the moving amounts in the positive direction of the Xc-axis, in the positive direction of the Yc-axis, and in the positive direction of the Zc-axis correspond to the moving amounts in the positive direction of the Xwd-axis, in the positive direction of the Ywd-axis, and in the positive direction of the Zwd-axis, respectively. Further, the rotations and the rotating directions on the Xc-axis, the Yc-axis, and the Zc-axis correspond to the rotations and the rotating directions on the Xwd-axis, the Ywd-axis, and the Zwd-axis, respectively, and the constant (Kr) multiples of the rotation amounts on the Xc-axis, the Yc-axis, and the Zc-axis correspond to the rotation amounts on the Xwd-axis, the Ywd-axis, and the Zwd-axis, respectively.

Therefore, when the object coordinate system Cwp is moved to the object coordinate system Cwd, the second determinator 20f determines a relationship similar to the relationship between the object coordinate system Cwp before the movement and the manipulation coordinate system Cc as the new second coordinate system relationship 20pb (that is, maintains the second coordinate system relationship 20pb before and after the movement).

The first operational commander 20g performs a calculation for converting the information in the manipulation coordinate system Cc into the information in the robot coordinate system Cr based on the first coordinate system relationship 20pa and the second coordinate system relationship 20pb, and outputs the operational command including the converted information to the motion controller 20i. In detail, the first operational commander 20g receives the manipulation command from the operation input device 40, and converts the manipulational position command and the manipulational force command in the manipulation coordinate system Cc included in the manipulation command, into position command and force command in the robot coordinate system Cr. For example, the first operational commander 20g uses the expression "Cwd=M1d·Cr" and the expression "Cwd=M2·Cc," to calculate the expression "M1d·Cr=M2·Cc" and further calculate the expression "Cr=M1d$^{-1}$M2·Cc." The first operational commander 20g inputs the manipulational position command and the manipulational force command into the expression "Cr=M1d$^{-1}$M2·Cc" to calculate the position command and the force command of the end effector 11 in the robot coordinate system Cr. The first operational commander 20g outputs the operational command including the position command and the force command of the end effector 11 to the motion controller 20i.

Note that, in this embodiment, the robot coordinate system Cr is the same as the world coordinate system. However, when the robot coordinate system Cr differs from the world coordinate system, the first operational commander 20g may convert the information in the manipulation coordinate system Cc into the information in the robot coordinate system Cr by further using the relationship between the robot coordinate system Cr and the world coordinate system.

Here, the position command of the end effector 11 indicates the position of the end effector 11. The force command of the end effector 11 indicates the force which the end effector 11 applies to the object. The position command may include a command of the three-dimensional position and the three-dimensional posture of the end effector 11. The position command may include an execution time of the command of the three-dimensional position and the three-dimensional posture. The force command may include a command of a magnitude and a direction of the force. Further, the force command may include the execution time of the command of the magnitude and the direction of the force. The three-dimensional posture is a posture in the three-dimensional space. In this specification and the claims, the "force" may include at least the magnitude of the force among the magnitude and the direction of the force, and the "position" may include at least the three-dimensional position among the three-dimensional position and the three-dimensional posture. Further, the operational command may include a command for driving or stopping the drive of the grinding device 11a.

The motion controller 20i generates a control command for operating each part of the robot 10 according to the operational command, and outputs it to the robot 10. The motion controller 20i acquires information on an operating state of each part of the robot 10 from the operational information processor 20j, and generates a control command by using this information as feedback information. In detail, the motion controller 20i generates a control command for operating the servomotors Ma of the arm drives M1, M2, M3, M4, M5, and M6 of the robotic arm 12, and a motor (not illustrated) of the grinding device 11a of the end effector 11.

The operational information processor 20j detects and processes operational information of the robot 10. The operational information processor 20j detects an ON state and an OFF state of the grinding device 11a as operational information based on the power supplying state etc. of the grinding device 11a. The operational information processor 20j acquires, as the operational information, a detection value of the rotation sensor Mb of the servomotor Ma of each of the arm drives M1, M2, M3, M4, M5, and M6, a detection value of the current sensor Mc of the servomotor Ma, and a detection value of the force sensor 11e of the end effector 11. Note that the operational information processor 20j may acquire, as the operational information, the command value of the current which the drive circuit of the servomotor Ma supplies to the servomotor Ma. The operational information processor 20j outputs, as the feedback information, the operational information described above to the motion controller 20i and the second operational commander 20h.

In order to give the reaction force against the operating force by the user P to the gripper 401 of the user interface 400, the second operational commander 20h generates a motor operational command which is a command for operating each motor 404 by using the operational information received from the operational information processor 20j, and outputs it to the operation input device 40. In detail, the second operational commander 20h generates a motor operational command for each motor 404 to give, to the gripper 401, a reaction force corresponding to the magnitude and the direction of the force detected by the force sensor 11e, which is the force data included in the operational information. Note that the second operational commander 20h may generate the motor operational command of each motor 404 to move the gripper 401 to the position and the posture corresponding to the position and the posture of the end effector 11, which is the position data included in the operational information. Note that the second operational commander 20h may output, to the operation input device 40, the commands for the reaction force, the position, and the posture which are given to the gripper 401, and the operation control device 420 may generate the motor operational command based on this command.

[Operation of Robot System]
[Operation of Robot by Manipulation of Operation Input Device]

Operation of the robot 10 by manipulation of the user interface 400 of the operation input device 40 is described. As illustrated in FIGS. 1 and 3, for example, the user P grips the handles 401a and 401b of the gripper 401 and moves and changes the posture of the gripper 401 in the moving direction to a target position of the grinding device 11a of the end effector 11, and in the rotating direction to a target posture. Further, the user P gives an input to the input part 401c of the gripper 401 to start the grinding device 11a.

The support 402 moves and changes the posture together with the gripper 401, and causes each of the six arms 403 to perform operation, such as bending and changing the posture to rotate the rotation shaft of the motor 404 connected to the arm 403. The operation control device 420 outputs, to the control device 20, the manipulation command based on the rotation signal of the rotation sensor of the motor 404 and the force signal of the force sensor 405.

The control device 20 generates the operational command etc. based on the manipulation command, and causes the robot 10 to operate according to the operational command etc. The control device 20 operates the robotic arm 12 so that the change in the position and the change in the posture of the end effector 11, and the applied force to the object W through the grinding device 11a reflect the force signal described above. Therefore, the user P can operate the gripper 401 of the user interface 400 to cause the robot 10 to perform operation as he/she intended.

Further, the control device 20 causes each motor 404 to generate the rotational load (may also be referred to as the "load torque") corresponding to the reaction force, in order to give to the gripper 401 the reaction force corresponding to the force data based on the detection signal of the force sensor 11e of the end effector 11. Therefore, for example, the user P can operate the position and the posture of the gripper 401, while sensing the reaction force from the gripper 401 as if he/she receives the reaction force from the object W.

The reaction force of the gripper 401 reflects the magnitude and the direction of the force which are detected by the force sensor 11e. Such a reaction force of the gripper 401 can make the hands of the user P sense the state of the grinding device 11a during operation which is different according to the surface state of the object. For example, the reaction force of the gripper 401 can make the hands of the user P feel the tactile sense which should be received by the hands of the user P when the user P performs grinding with his/her hands holding the grinding device 11a. Further, the reaction force of the gripper 401 may make the hands of the user P feel vibration of the grinding device 11a during operation.

The commands of the amount of change in the position, the amount of change in the posture, and the magnitude of the action force of the end effector 11 are proportionally increased to the commands of the amount of change in the position, the amount of change in the posture, and the magnitude of the force which are indicated by the force signal of the force sensor 405. Therefore, the robotic arm 12 can change the position and the posture of the end effector 11 greatly beyond the operational range of the gripper 401. Further, the end effector 11 can generate the action force greatly beyond the force applied to the gripper 401.

[Operation of Robot System in Control Mode of Automatic Change of Object Coordinate System]

Figure 9:
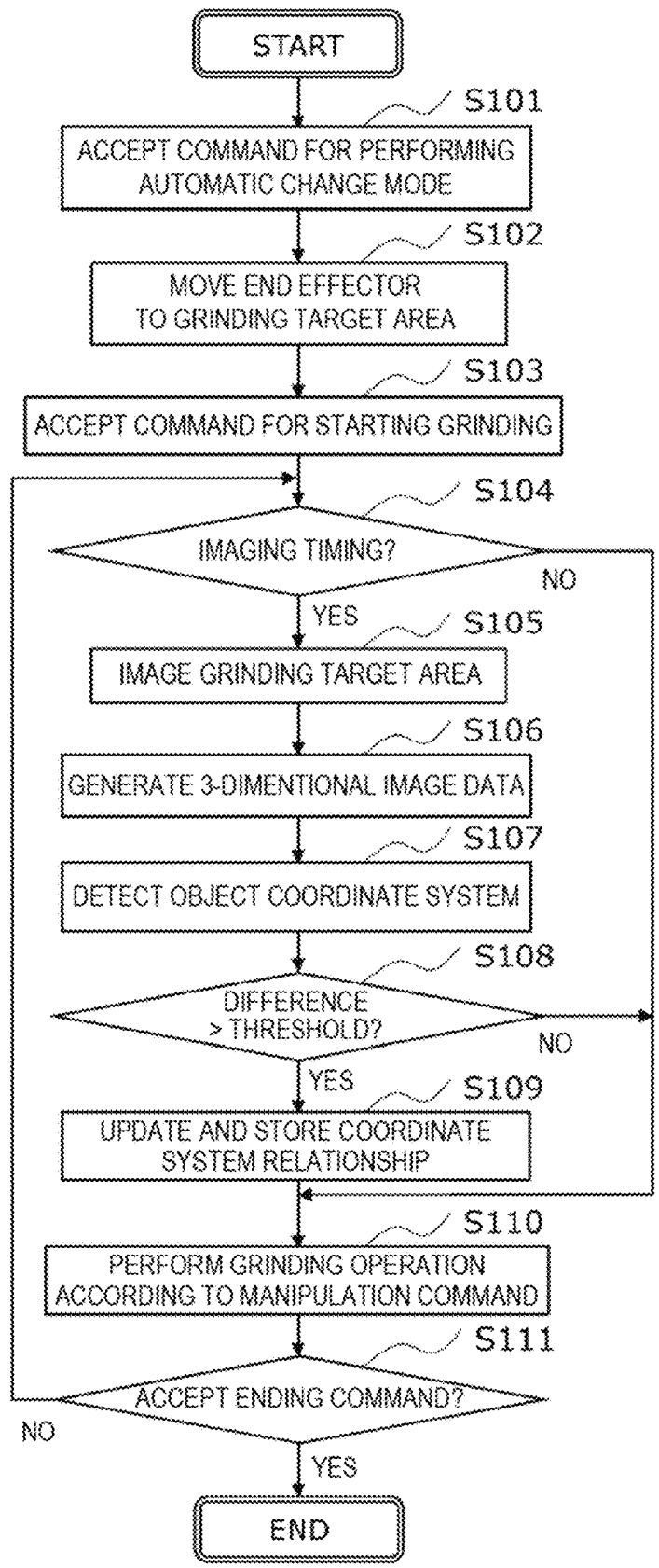
FIG. 9 is a flowchart illustrating one example of operation of the robot system according to this embodiment.

Operation of the robot system 1 in a control mode in which the object coordinate system is changed automatically is described. FIG. 9 is a flowchart illustrating one example of operation of the robot system 1 according to this embodiment.

As illustrated in FIG. 9, at Step S101, the user P inputs, into the input device 410 of the operation input device 40, a command for performing an automatic change mode which is a control mode in which the object coordinate system is changed automatically, and the operation control device 420 accepts this command and outputs it to the control device 20.

Next, at Step S102, the control device 20 causes the robotic arm 12 to move the end effector 11 in front of the grinding target area WA of the object W according to the manipulation command of the user interface 400 inputted by the user P.

Next, at Step S103, the user P inputs a command for starting grinding into the input device 410, and the operation control device 420 accepts this command and outputs it to the control device 20.

Next, at Step S104, the control device 20 determines whether it is an imaging timing of the imaging device 30, and if it is the imaging timing (Yes at Step S104), it transits to Step S105, and if it is not the imaging timing (No at Step S104), it transits to Step S110. Note that, at Step S104 next to Step S103, it is the imaging timing. The control device 20 may be provided with a timer or a clock which measures time, and may measure an imaging timing for every given time period.

At Step S105, the control device 20 causes the imaging device 30 to image the grinding target area WA. Next, at Step S106, the control device 20 processes the image data of the grinding target area WA to generate the three-dimensional image data of the image data. Next, at Step S107, the control device 20 detects a new object coordinate system Cwd by using the three-dimensional image data.

Next, at Step S108, the control device 20 determines whether the difference between the new object coordinate system Cwd and the current object coordinate system Cwp is above the threshold. If above the threshold (Yes at Step S108), the control device 20 transits to Step S109, and if below the threshold (No at Step S108), it transits to Step S110.

At Step S109, the control device 20 updates the first coordinate system relationship 20pa and the second coordinate system relationship 20pb which are to be stored in the memory 20p based on the new object coordinate system Cwd, and stores them in the memory 20p.

Next, at Step S110, the control device 20 operates the robotic arm 12 according to the manipulation command of the user interface 400 inputted by the user P, and the first coordinate system relationship 20pa and the second coordinate system relationship 20pb in the memory 20p to cause the grinding device 11a of the end effector 11 to grind the grinding target area WA.

Next, at Step S111, the control device 20 determines whether it accepted the command for ending the grinding work via the input device 410, and if it accepted (Yes at Step S111), it ends the series of processings, and if not accepted (No at Step S111), it returns to Step S104.

From the above, when the position and/or the posture of the grinding target area WA are changed with the progress of grinding work, the control device 20 repeats the processings from Step S104 to Step S111 to move the object coordinate system Cw, and updates the first coordinate system relationship 20pa and the second coordinate system relationship 20pb according to the object coordinate system Cw. The control device 20 controls the operation of the robot 10 according to the manipulation command inputted into the user interface 400 based on the first coordinate system relationship 20pa and the second coordinate system relationship 20pb which are updated. Further, the control device 20 can detect the changes in the position and/or the posture of the grinding target area WA for every given time period, and update the first coordinate system relationship 20pa and the second coordinate system relationship 20pb corresponding to the state of the grinding target area WA.

For example, depending on the length of the given time period, the control device 20 can update the first coordinate system relationship 20*pa* and the second coordinate system relationship 20*pb* corresponding to the state of the grinding target area WA on real time.

Figure 10:
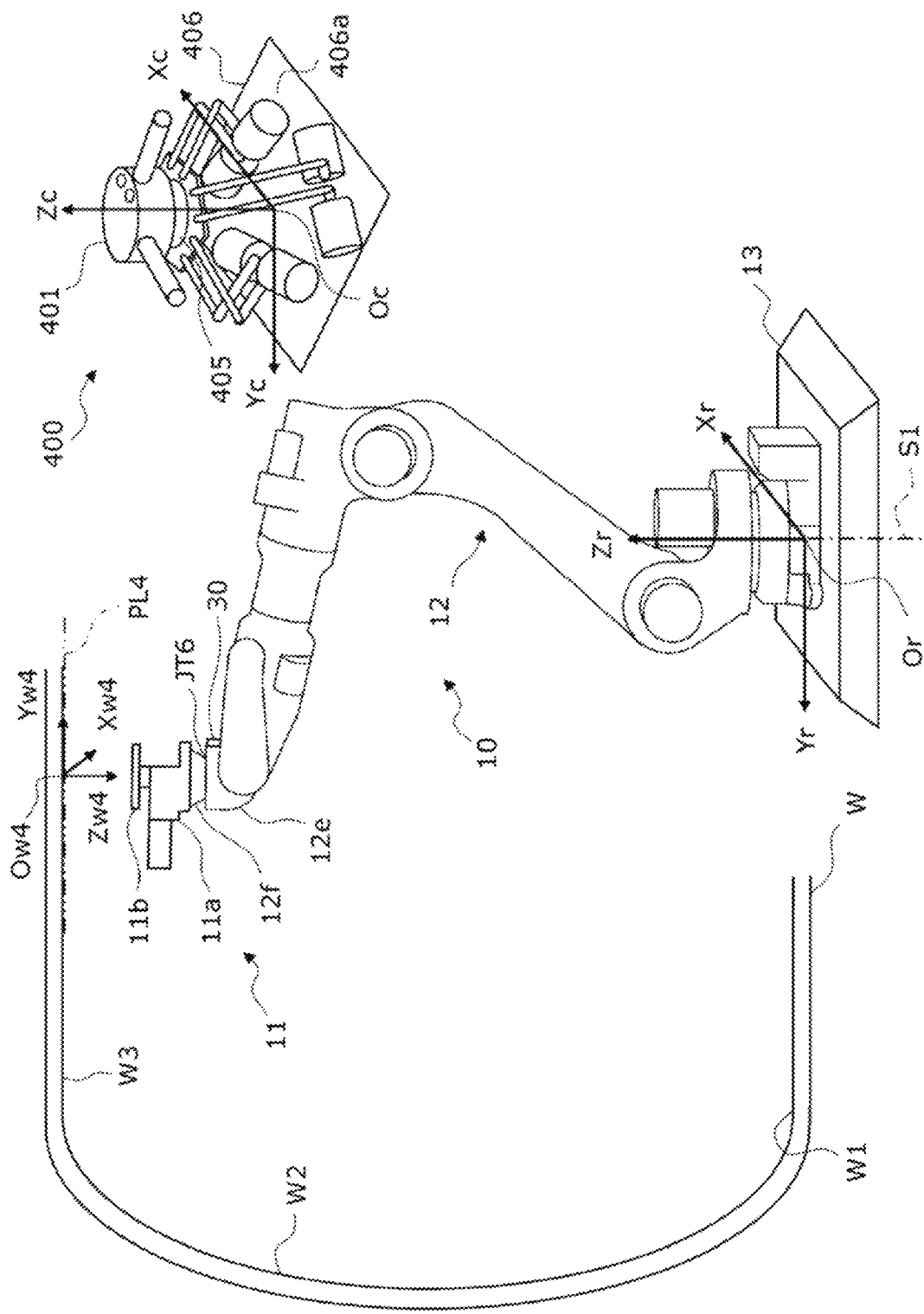
FIG. 10 is a view illustrating one example of movement in each coordinate system of the robot system of FIG. 6.

For example, the object coordinate system Cw1 of FIG. 6 can be moved to the object coordinate system Cw2 of FIG. 7 and an object coordinate system Cw4 of FIG. 10. Note that FIG. 10 is a view illustrating one example of the movement in each coordinate system of the robot system 1 of FIG. 6. The object coordinate system Cw4 is a coordinate system in which an inner surface W3 of the ceiling of the object W is used as a reference plane PL4. Therefore, in each case of FIGS. 6, 7, and 10, for example, when the user P applies a force to the gripper 401 of the user interface 400 in the positive direction of the Yc-axis, the control device 20 causes the robot 10 to move the end effector 11 in the positive direction of the Yw1-axis, the positive direction of the Yw2-axis, and the positive direction of the Yw4-axis. Therefore, even when the position and/or the posture of the grinding target area WA which is the target to which the robot 10 applies operation changes, the user P can operate the user interface 400, without changing the posture.

[Operation of Robot System in Control Mode of Non-automatic Change of Object Coordinate System]

Figure 11:
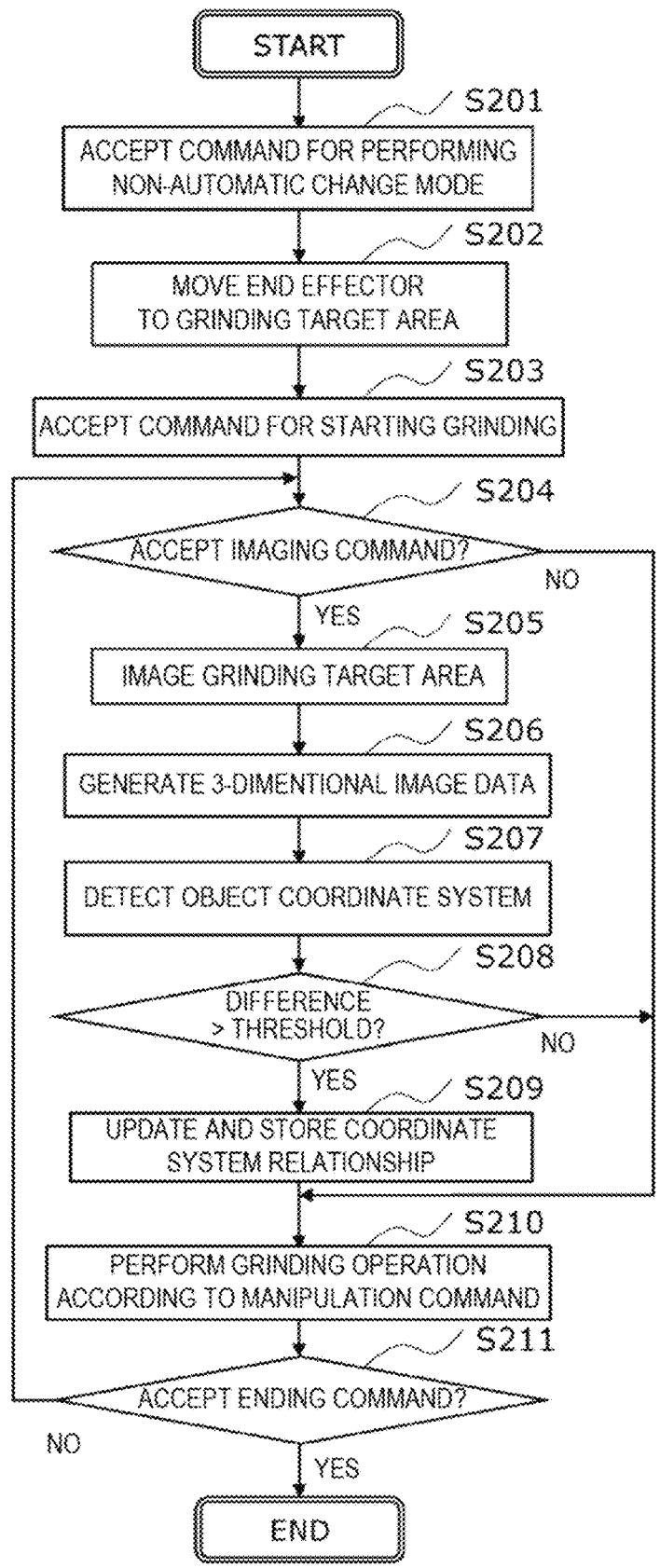
FIG. 11 is a flowchart illustrating one example of operation of the robot system according to this embodiment.

Operation of the robot system 1 in a control mode in which the object coordinate system is not changed automatically is described. FIG. 11 is a flowchart illustrating one example of the operation of the robot system 1 according to this embodiment.

As illustrated in FIG. 11, at Step S201, the user P inputs, into the input device 410 of the operation input device 40, a command for performing a non-automatic change mode which is a control mode in which the object coordinate system is not changed automatically, and the operation control device 420 accepts this command and outputs it to the control device 20.

Next, at Step S202, the control device 20 causes the robotic arm 12 to move the end effector 11 to a location in front of the grinding target area WA of the object W according to the manipulation command of the user interface 400 inputted by the user P.

Next, at Step S203, the user P inputs, into the input device 410, a command for starting the grinding, and the operation control device 420 accepts this command and outputs it to the control device 20.

Next, at Step S204, the control device 20 determines whether it accepted the command for causing the imaging device 30 to image via the input device 410, and if it accepted (Yes at Step S204), it transits to Step S205, and if not accepted (No at Step S204), it transits to Step S210. Note that, at Step S204 next to Step S203, the user P inputs an imaging command into the input device 410.

Processings from Step S205 to Step S210 are similar to the processings from Step S105 to S110, respectively.

Next, at Step S211, the control device 20 determines whether it accepted a command for ending the grinding work via the input device 410, and if it accepted (Yes at Step S211), it ends the series of processings, and if not accepted (No at Step S211), it returns to Step S204.

From the above, when accepted via the input device 410 the command for causing the imaging device 30 to image, the control device 20 detects the object coordinate system Cw, and updates the first coordinate system relationship 20*pa* and the second coordinate system relationship 20*pb* corresponding to the change in the position and/or the posture of the object coordinate system Cw. That is, the control device 20 updates the first coordinate system relationship 20*pa* and the second coordinate system relationship 20*pb* corresponding to the demand of the user P. Then, the control device 20 controls the operation of the robot 10 according to the manipulation command inputted into the user interface 400 based on the first coordinate system relationship 20*pa* and the second coordinate system relationship 20*pb* which are updated.

Note that, by incorporating the processings from Step S204 to Step S205 into the processing from Step S101 to Step S111, the control device 20 may update the first coordinate system relationship 20*pa* and the second coordinate system relationship 20*pb* corresponding to the demand of the user P also in the automatic change mode.

Other Embodiments

As described above, although examples of the embodiment of the present disclosure are described, the present disclosure is not limited to the above embodiment. That is, various modifications and improvements are possible within the scope of the present disclosure. For example, those obtained by variously modifying the embodiment, and those constructed by combining the components in different embodiments are also encompassed within the scope of the present disclosure.

For example, although in this embodiment the control device 20 detects the object coordinate system using the three-dimensional image data of the object, it is not limited to this configuration. For example, information on a plurality of object coordinate systems, such as the object coordinate systems Cw1, Cw2, Cw3, and Cw4 may be set and stored beforehand in the memory 20*p*. The control device 20 may read, from the memory 20*p*, the object coordinate system specified by the user P via the operation input device 40, and may update the first coordinate system relationship 20*pa* and the second coordinate system relationship 20*pb* by using this object coordinate system.

Further, in the above embodiment, the control device 20 continuously detects the change in the position and/or the posture of the grinding target area WA based on the three-dimensional image data of the grinding target area WA imaged at the given time period, and changes the object coordinate system corresponding to the state of the grinding target area WA. Alternatively, the control device 20 changes the object coordinate system corresponding to the state of the grinding target area WA, based on the three-dimensional image data of the grinding target area WA which is imaged at the given timing which is a timing at which a command is inputted via the operation input device 40. However, the timing for changing the object coordinate system is not limited to the timing described above.

For example, the control device 20 may cause the imaging device 30 to image the grinding target area WA at a given timing, such as a given timing corresponding to the progress of grinding work of the grinding target area WA, and a given timing set in time beforehand, and may change the object coordinate system corresponding to the state of the grinding target area WA based on the three-dimensional image data of the grinding target area WA. For example, the progress of grinding work may be progress of the ground area, progress of grinding in a given direction, progress of grinding work time, etc.

Although the robot system 1 according to the above embodiment is provided with the imaging device 30 as the distance detecting device, it is not limited to this configuration. The distance detecting device may be any device as long as it is detectable of the distance to the object. For example, the distance detecting device may be a sensor which detects the distance using light wave, laser, or ultrasonic wave.

Although in the above embodiment the robot 10 which is the industrial robot is illustrated as a mechanical apparatus to which the technology of the present disclosure is applicable, the mechanical apparatus to which the technology of the present disclosure is applicable may be mechanical apparatuses other than the industrial robot. For example, the mechanical apparatus may be a service robot, construction machinery, a tunnel boring machine, a crane, a cargo conveyance vehicle, and a humanoid. The service robot is a robot used in various service industries, such as nursing, medical science, cleaning, security, information service, rescue, cooking, and goods offering.

Alternatively, the technology of the present disclosure may be a controlling method. For example, the controlling method according to one embodiment of the present disclosure is a controlling method which controls the slave unit manipulated by the master unit. The method includes determining a first coordinate system relationship which is a relationship between an object coordinate system set to an object to be processed by the slave unit and an slave coordinate system set to the slave unit, determining a second coordinate system relationship which is a relationship between a master coordinate system set to the master unit and the object coordinate system, and outputting an operational command for causing the slave unit to operate with respect to the object, according to the operational information that is information inputted into the master unit by a force being applied to an operation end of the master unit, the first coordinate system relationship, and the second coordinate system relationship. When the object coordinate system is moved, the first coordinate system relationship after the movement is newly determined based on the moved object coordinate system and the slave coordinate system, and the second coordinate system relationship after the movement between the moved object coordinate system and the master coordinate system is determined as a relationship similar to the second coordinate system relationship before the movement. This controlling method may be realized by a circuit such as a CPU and an LSI, or an IC card, or a sole module.

Further, the technique of the present disclosure may be a program for performing the controlling method described above, or may be a non-transitory computer readable recording medium on which the program is recorded. It is needless to say that the program described above may be distributed via a transmission medium, such as the Internet.

Note that all the numbers used above, such as the order and the quantity are illustrated in order to concretely explain the technique of the present disclosure, and the present disclosure is not limited to the illustrated numbers. Further, the connection relationships between the components are illustrated in order to concretely explain the technique of the present disclosure, and the connection relationship which realizes the functions of the present disclosure is not limited to those relationships.

The division of a block in the functional block diagram is one example, and therefore, a plurality of blocks may be realized as one block, one block may be divided into a plurality of blocks, and/or a part of the function may be moved to other blocks. Further, functions of a plurality of blocks which have similar functions may be processed in parallel or in a time-divided manner by sole hardware or software.

The invention claimed is:

1. A system, comprising:
a camera;
an operation device including an operation end, and an operation detector that detects operational information that is information inputted by a force being applied to the operation end and outputs the operational information;
a robot including an end effector that applies an action to an object in a target area, and an arm that moves the end effector; and
a control device including circuitry configured to:
  determine that a timer has reached an image timing;
  in response to determination that the timer has reached the image timing:
    control the camera to capture an image of the target area;
    generate three-dimensional image data from the image:
    determine a first coordinate system relationship between a robot coordinate system set to the robot and an object coordinate system set to the object and store the first coordinate system relationship in a memory, wherein the object coordinate system is detected based on the three-dimensional image data;
    determine a second coordinate system relationship between an operation coordinate system set to the operation device and the object coordinate system and store the second coordinate system relationship in the memory;
  detect movement of the object indicating a change in the object coordinate system;
  determine that a first difference between an origin position of the object coordinate system prior to the change and the object position of the object coordinate system after the change is greater than a first threshold or that a second difference between a posture of the object coordinate system prior to the change and the posture of the object coordinate system after the change is greater than a second threshold; and
  in response to determination that the first difference is greater than the first threshold or the second difference is greater than the second threshold:
    adjust the object coordinate system;
    update the first coordinate system relationship and the second coordinate system relationship based on the adjustment to the object coordinate system; and then
    store the first coordinate system relationship and the second coordinate system relationship in the memory;
  receive the operational information in the operation coordinate system from the operation device;
  translate the operational information in the operation coordinate system to the robot coordinate system to generate an operational command in the robot coordinate system based on the first coordinate system relationship and the second coordinate system relationship; and
  output the operational command to the robot to control the end effector and the arm.

2. The system of claim 1, further comprising:
a distance detecting device including the camera, wherein the distance detecting device detects an object distance that is a distance to the object, and the circuitry is further configured to determine the object coordinate system based on the object distance.

3. The system of claim 2, wherein
the distance detecting device detects the object distance at a given time interval,
the circuitry determines that the object is moved based on the object distance, and
in response to determination that the object is moved, the circuitry updates the object coordinate system corresponding to the object distance.

4. The system of claim 2, wherein
the distance detecting device detects the object distance at a given timing,
the circuitry determines that the object is moved based on the object distance, and
in response to determination that the object is moved, the circuitry updates the object coordinate system corresponding to the object distance.

5. The system of claim 2, wherein
the camera captures the image from which a distance to a photographic subject is detected, and
the circuitry detects the object distance by image-processing the image.

6. The system of claim 1, wherein
the operation detector detects a direction and a magnitude of a force applied to the operation end as the operational information, and
the circuitry generates the operational command including a position and a posture of the end effector and an action force to the object.

7. The system of claim 6, wherein the operation detector detects magnitudes of forces in directions of three axes and moments of forces on the three axes applied to the operation end, as the operational information.

8. The system of claim 1, wherein
the end effector includes a grinding device, and
the arm is a robotic arm.

9. A method, comprising:
determining that a timer has reached an image timing;
in response to the determining indicating that the timer has reached the image timing:
controlling a camera to capture an image of the target area;
generating three-dimensional image data from the image;
determining a first coordinate system relationship between an object coordinate system and a robot coordinate system, wherein the object coordinate system is set to an object to be processed by a robot, the robot coordinate system is set to the robot, the robot includes an end effector that applies an action to the object, and the robot includes an arm that moves the end effector, and the object coordinate system is detected based on the three-dimensional image data;
storing the first coordinate system relationship in a memory;
determining a second coordinate system relationship between an operation coordinate system and the object coordinate system;
storing the second coordinate system relationship in the memory;
detecting movement of the object indicating a change in the object coordinate system;
determining that a first difference between an origin position of the object coordinate system prior to the change and the object position of the object coordinate system after the change is greater than a first threshold or that a second difference between a posture of the object coordinate system prior to the change and the posture of the object coordinate system after the change is greater than a second threshold; and
in response to determination that the first difference is greater than the first threshold or the second difference is greater than the second threshold:
adjusting the object coordinate system;
updating the first coordinate system relationship and the second coordinate system relationship based on the adjustment to the object coordinate system; and then
storing the first coordinate system relationship and the second coordinate system relationship in the memory;
receiving operational information in the operation coordinate system from an operation device, the operational information having been detected by an operation detector of the operation device, and the operational information being information input by a force applied to an operation end of the operation device;
translating the operational information in the operation coordinate system to the robot coordinate system to generate an operational command in the robot coordinate system based on the first coordinate system relationship and the second coordinate system relationship; and
outputting the operational command to the robot to control the end effector and the arm.

10. The system of claim 3, wherein
the camera captures the image from which a distance to a photographic subject is detected, and
the control device further includes an image processor that detects the object distance by image-processing the image.

11. The system of claim 4, wherein
the camera captures the image from which a distance to a photographic subject is detected, and
the control device further includes an image processor that detects the object distance by image-processing the image.

12. The system of claim 1, wherein each of the robot coordinate system, the object coordinate system and the operation coordinate system are three-dimensional coordinate systems.

13. The system of claim 1, wherein the circuitry is configured to
determine a three-dimensional position of the object based on the image, and
detect whether the object has moved based on the three-dimensional position of the object.

14. The system of claim 13, wherein the circuitry is further configured to
determine the posture of the object based on the image, and
determine whether the change in the posture is detected based on the determined posture.

* * * * *